(12) United States Patent
Harlan et al.

(10) Patent No.: US 8,304,389 B2
(45) Date of Patent: *Nov. 6, 2012

(54) METHODS OF INHIBITING CELL DEATH OR INFLAMMATION IN A MAMMAL BY ADMINISTERING A BCL PROTEIN

(75) Inventors: John M. Harlan, Seattle, WA (US); Robert K. Winn, Bainbridge Island, WA (US); Akiko Iwata, Seattle, WA (US); Joan Tupper, Seattle, WA (US); John Li, San Francisco, CA (US)

(73) Assignee: University of Washington through its Center for Commercialization, a Public Institution of Higher Education, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/107,866

(22) Filed: May 13, 2011

(65) Prior Publication Data

US 2011/0312901 A1    Dec. 22, 2011

Related U.S. Application Data

(62) Division of application No. 11/576,591, filed as application No. PCT/US2005/035666 on Oct. 4, 2005, now Pat. No. 7,964,565.

(60) Provisional application No. 60/709,053, filed on Aug. 16, 2005, provisional application No. 60/714,511, filed on Oct. 4, 2004.

(51) Int. Cl.
*A61K 38/16* (2006.01)

(52) U.S. Cl. ....... 514/18.7; 514/1.1; 514/21.2; 514/21.3

(58) Field of Classification Search .................. None
See application file for complete search history.

(56) References Cited

U.S. PATENT DOCUMENTS

| 5,523,393 | A  |   | 6/1996 | Tsujimoto et al. |         |
|-----------|----|---|--------|------------------|---------|
| 7,521,548 | B2 |   | 4/2009 | Reed et al.      |         |
| 7,964,565 | B2 | * | 6/2011 | Harlan et al.    | 514/18.7 |
| 2003/0176671 | A1 |   | 9/2003 | Reed et al.     |         |

FOREIGN PATENT DOCUMENTS

| EP | 1241254 A1 | 9/2002 |
| WO | WO 97/30083 A1 | 8/1997 |
| WO | WO 03/031650 A2 | 4/2003 |
| WO | WO 2004/039956 A2 | 5/2004 |
| WO | WO 2006/041835 A2 | 4/2006 |

OTHER PUBLICATIONS

Mikayama et al. Proc. Natl. Acad. Sci. USA, vol. 90, pp. 10056-10060 (1993).*
Voet et al. Biochemistry John Wiley & Sons, Inc., pp. 126-128 and 228-234 (1990).*
Chao, D.T. et al., "BCL-2 Family: Regulators of Cell Death," Annual Review of Immunology, Jan. 1998, pp. 395-419, vol. 16.
European Examination Report, European Application No. 05802454.8, May 3, 2012, 5 pages.
United States Office Action, U.S. Appl. No. 12/514,436, Feb. 23, 2012, 7 pages.
United States Office Action, U.S. Appl. No. 12/697,982, Apr. 16, 2012, 14 pages.
Adams, J.M. et al., "The Bcl-2 Protein Family: Arbiters of Cell Survival," Science, 1998, pp. 1322-1326, vol. 281.
Australian Examiner's First Report, Australian Application No. 2005294453, Apr. 15, 2009, 2 pages.
Australian Examiner's Second Report, Australian Application No. 2005294453, Nov. 10, 2010, 2 pages.
Boise, L.H. et al., "bcl-x, a bcl-2-Related Gene That Functions as a Dominant Regulator of Apoptotic Cell Death," Cell, Aug. 27, 1993, pp. 597-608, vol. 74.
Cantara, S. et al., "Exogenous BH4/Bcl-2 Peptide Reverts Coronary Endothelial Cell Apoptosis Induced by Oxidative Stress," Journal of Vascular Research, Mar. 19, 2004, pp. 202-207, vol. 41.
Cao, Y-J. et al., "Liposome-Mediated Transfer of the Bcl-2 Gene Results in Neuroprotection After In Vivo Transient Focal Cerebral Ischemia in an Animal Model," Gene Therapy, 2002, pp. 415-419, vol. 9.
Cao, G. et al., "In Vivo Delivery of Bcl-xl Fusion Protein Containing the TAT Protein Transduction Domain Protects Against Ischemic Brain Injury and Neuronal Apoptosis," Journal of Neuroscience, Jul. 1, 2002, pp. 5423-5431, vol. 22, No. 13, New York, NY, USA.
Chen, Z. et al., "Overexpression of Bcl-2 Attenuates Apoptosis and Protects Against Myocardial I/R Injury in Transgenic Mice," Am. J. Physiol. Heart Circ. Physiol., 2001, pp. H2313-H2320, vol. 280.
Chinese Office Action, Chinese Application No. 200580041661.8, Jul. 10, 2009, 15 pages.
Choi, S.S. et al., "Bfl-1, a Bcl-2-related Gene, is the Human Homolog of the Murine A1, and Maps to Chromosome 15q24.3," Mammalian Genome, 1997, pp. 781-782, vol. 8.
Coopersmith, C.M. et al., "Overexpression of Bcl-2 in the Intestinal Epithelium Improves Survival in Septic Mice," Crit. Care Med., 2002, pp. 195-201, vol. 30, No. 1.
Cory, S. et al., "The Bcl-2 Family: Roles in Cell Survival and Oncogenesis," Oncogene, 2003, pp. 8590-8607, vol. 22.
D'Sa-Eipper, C. et al., "Functional Dissection of Bfl-1, a Bcl-2 Homolog: Anti-Apoptis, Oncogene-Cooperation and Cell Proliferation Activities," Oncogene, 1998, pp. 3105-3114, vol. 16.
European Extended Search Report, European Application No. 05802454.8, Oct. 6, 2009, 12 pages.
European Examination Report, European Application No. 05802454.8, Feb. 2, 2010, 1 page.
European Examination Report, European Application No. 05802454.8, Apr. 7, 2011, 6 pages.
Gibson, L. et al., "bcl-w, a Novel Member of the bcl-2 Family, Promotes Cell Survival," Oncogene, 1996, pp. 665-675, vol. 13.

(Continued)

*Primary Examiner* — Prema Mertz
(74) *Attorney, Agent, or Firm* — Fenwick & West LLP

(57) ABSTRACT

In one aspect the present invention provides methods for inhibiting cell death or inflammation in a mammal, wherein the methods each include the step of administering to a mammal a Bcl protein in an amount sufficient to inhibit cell death or inflammation in the mammal. The invention also provides methods for identifying a Bcl protein that inhibits cell death or inflammation when administered to a mammal.

20 Claims, 6 Drawing Sheets

OTHER PUBLICATIONS

Hockenbery, D.M. et al., "Bcl-2 Functions in an Antioxidant Pathway to Prevent Apoptosis," Cell, Oct. 22, 1993, pp. 241-251, vol. 75.

Hockenbery, D.M. et al., "Bcl-2 is an Inner Mitochondrial Membrane Protein That Blocks Programmed Cell Death," Nature, 1990, pp. 334-336, vol. 348.

Hotchkiss, R.S. et al., "Overexpression of Bcl-2 in Transgenic Mice Decreases Apoptosis and Improves Survival in Sepsis," The Journal of Immunology, 1999, pp. 4148-4156, vol. 162.

Iwata, A. et al., "Over-Expression of Bcl-2 Provides Protection in Septic Mice by a *trans* Effect," The Journal of Immunology, 2003, pp. 3136-3141, vol. 171.

Japanese Office Action, Japanese Application No. 2007-534888, May 30, 2011, 13 pages.

Karsan, A. et al., "Cloning of Human Bcl-2 Homologue: Inflammatory Cytokines Induce Human A1 in Cultured Endothelial Cells," Blood, Apr. 15, 1996, pp. 3089-3096, vol. 87, No. 8.

Katsura, K., Application of New Protein Therapy to Cerebral Infarction, Dec. 15, 2002, J. Nippon Med. Sch., Japan, pp. 551-552, vol. 70, No. 6.

Lee, L.C. et al., Evidence for .alpha.-Helical Conformation of an Essential N-terminal Region in the Human Bcl2 Protein, The Journal of Biological Chemistry, Sep. 20, 1996, pp. 23284-23288, vol. 271, No. 38.

Lin, E.Y. et al., Characterization of A1, a Novel Hemopoietic-Specific Early-Response Gene with Sequence Similarity to bcl-2.sup.1, The Journal of Immunology, Aug. 15, 1993, pp. 1979-1988, vol. 151.

Ono, M. et al., "BH4 Peptide Derivative from Bcl-xL Attenuates Ischemia/Reperfusion Injury Through Anti-Apoptotic Mechanism in Rat Hearts," European Journal of Cardio-Thoracic Surgery, Jan. 2005, pp. 117-121, vol. 27, Issue 1.

PCT International Search Report and Written Opinion, PCT/US05/35666, Mar. 6, 2007, 8 pages.

PCT International Search Report and Written Opinion, PCT Application No. PCT/US2007/084052, Jul. 31, 2009, 19 pages.

PCT Invitation to Pay Additional Fees, PCT/US2007/084052, May 18, 2009, 10 pages.

Reynolds, J.E. et al., "Bcl-2 and MCl-1 Expression in Chinese Hamster Ovary Cells Inhibits Intracellular Acidification and Apoptosis Induced by Staurosporine," Experimental Cell Research, 1996, pp. 430-436, vol. 225.

Rocha, E., "The BH4 Domain of A1, an Anti-Apoptotic bcl Family Gene, is Necessary and Sufficient for its Antiinflammatory Function in Endothelial Cells," Transplantation Proceedings, 2001, p. 314, vol. 33.

Sentman, C.L. et al., "Bcl-2 Inhibits Multiple Forms of Apoptosis but not Negative Selection in Thymocytes," Cell, Nov. 29, 1991, pp. 879-888, vol. 67.

Stroka, D. M. et al., "Overexpression of A1, an NF.kappa.B-Inducible Anti-Apoptotic Bcl Gene, Inhibits Endothelial Cell Activation," Blood, Jun. 11, 1999, pp. 3803-3810, vol. 93, No. 11.

United States Office Action, U.S. Appl. No. 12/697,978, Jan. 4, 2012, 20 pages.

United States Office Action, U.S. Appl. No. 11/576,591, Jun. 15, 2010, 19 pages.

United States Office Action, U.S. Appl. No. 11/576,591, Dec. 8, 2010, 14 pages.

Werner, A.B. et al., "Bcl-2 Family Member Bfl-1/A1 Sequesters Truncated Bid to Inhibit Its Collaboration with Pro-apoptotic Bak or Bax," The Journal of Biological Chemistry, Jun. 21, 2002, pp. 22781-22788, vol. 277, No. 25.

Yin, W. et al., "TAT-Mediated Delivery of Bcl-xl Protein is Neuroprotective Against Neonatal Hypoxic-Ischemic Brain Injury Via Inhibition of Caspases and AIF," Neurobiology of Disease, Feb. 1, 2006, pp. 358-371, vol. 21, No. 2, Blackwell Scientific Publications, Oxford, GB.

Zhang, H. et al., "Structural Basis of BFL-1 for Its Interaction with Bax and Its Antiapoptotic Action in Mammalian and Yeast Cells," The Journal of Biological Chemistry, Apr. 14, 2000, pp. 11092-11099, vol. 275, No. 15.

\* cited by examiner

METHODS OF INHIBITING CELL DEATH OR INFLAMMATION IN A MAMMAL BY ADMINISTERING A BCL PROTEIN

STATEMENT REGARDING FEDERALLY SPONSORED RESEARCH OR DEVELOPMENT

This invention was made with government support under grant numbers GM66197, GM42686, and HL72262 awarded by National Institutes of Health. The government has certain rights in the invention.

FIELD OF THE INVENTION

The present invention relates to the use of exogenously administered proteins (such as Bcl-2 proteins) to inhibit cell death and/or inflammation.

BACKGROUND OF THE INVENTION

Programmed cell death is a normal and necessary part of mammalian development. For example, the development of separate fingers in a human fetus requires the programmed cell death of tissue between the developing fingers. The biochemical processes that cause programmed cell death may be triggered, however, by a variety of diseases and injuries. For example, programmed cell death may be triggered by traumatic injury, stroke, myocardial infarction, organ transplantation, and mesenteric and peripheral vascular disease. The programmed cell death further undermines the health of the injured or diseased organism.

Each of the foregoing types of diseases and injuries typically include some ischemia and reperfusion injury, which occurs when previously interrupted blood flow is restored to living tissue. For example, blockage of a coronary artery may cause cardiac muscle death due to the temporary lack of blood supply to the cardiac tissue. Additional muscle may die when blood flow is restored to the cardiac muscle by the administration of thrombolytic drugs.

Chronic and acute inflammation can also damage or kill living cells in a mammal. For example, the inflammation associated with emphysema causes lung damage over time. Inflammation may trigger programmed cell death, or may damage living tissue by some other mechanism. Accordingly, there is a continuing need for methods and compositions for inhibiting cell death and/or inflammation in a mammal.

SUMMARY OF THE INVENTION

In accordance with the foregoing, in one aspect the present invention provides methods for inhibiting cell death and/or inflammation in a mammal, wherein the methods each include the step of administering to a mammal a Bcl protein in an amount sufficient to inhibit cell death and/or inflammation in the mammal. The methods of this aspect of the invention can be used, for example, to treat injuries or diseases, in a mammal, that involve cell death (e.g., ischemia-reperfusion injury), and/or to treat injuries or diseases, in a mammal, that involve inflammation (e.g., asthma). The methods of this aspect of the invention can also be used, for example, to prophylactically treat a mammal to prevent or delay the onset of cell death and/or inflammation.

In another aspect, the present invention provides methods for identifying a Bcl protein that inhibits cell death and/or inflammation when administered to a mammal, wherein the methods of this aspect of the invention each include the step of screening a plurality of proteins to identify a Bcl protein that inhibits cell death and/or inflammation when administered to a mammal. The methods of this aspect of the invention can be used, for example, to identify Bcl proteins that inhibit cell death and/or inflammation when administered to a mammal, and that can be used to treat injuries or diseases, in a mammal, that involve cell death and/or inflammation.

In a further aspect, the present invention provides methods for identifying a Bcl protein that inhibits cell death and/or inflammation when administered to a mammal, wherein the methods of this aspect of the invention each include the step of analyzing data obtained from an experiment wherein a plurality of proteins are screened to identify a Bcl protein that inhibits cell death and/or inflammation in a mammal. The methods of this aspect of the invention can be used, for example, to identify Bcl proteins that inhibit cell death and/or inflammation when administered to a mammal, and that can be used to treat injuries or diseases, in a mammal, that involve cell death and/or inflammation.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
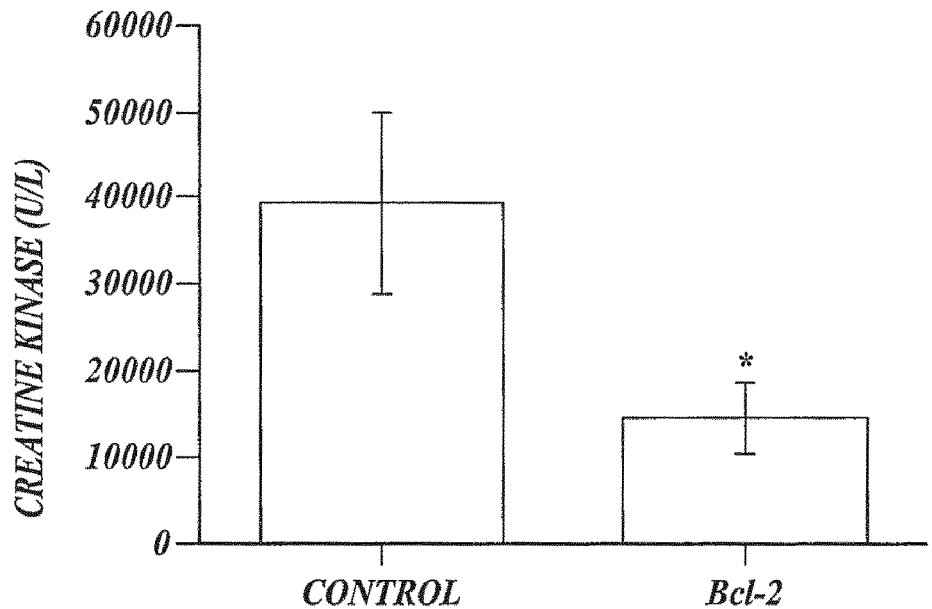
FIG. 1 shows a bar chart of creatine kinase concentration in blood plasma of eleven transgenic mice that expressed exogenous human Bcl-2 (hBcl-2) in their myeloid cells (identified as Bcl-2 in FIG. 1), and a bar chart of creatine kinase concentration in blood plasma of nine non-transgenic, control, C57BL/6 mice that did not express exogenous hBcl-2 in their myeloid cells. Creatine kinase concentration was measured after the mice had been subjected to ischemia-reperfusion injury as described in Example 1. Creatine kinase concentration is expressed in units per liter (U/L) ($*p<0.05$).

In one aspect, the present invention provides methods for inhibiting cell death in a mammal and/or inhibiting inflammation in a mammal. Each of the methods includes the step of administering to a mammal a Bcl protein in an amount sufficient to inhibit cell death and/or inflammation in the mammal.

Inhibition of cell death in a mammal encompasses complete or partial inhibition of cell death in a mammal. Inhibition of inflammation in a mammal encompasses complete or partial inhibition of inflammation in a mammal.

The methods of the present invention can be practiced on any mammal, such as primates (e.g., human beings), mammals of the genus *Canis* (e.g., domestic dog), mammals of the genus *Felis* (e.g., domestic cat), cattle, sheep, horses, goats and pigs.

In the practice of the present invention one or more types of Bcl proteins can be administered to a mammal suffering from cell death (e.g., suffering from a disease that causes cell death, or undergoing a medical treatment that causes cell death, or suffering from an injury that causes cell death). Examples of diseases, or medical treatments, that cause cell death include stroke, myocardial infarction, cardiac arrest, acute coronary syndrome/unstable angina, cardio-pulmonary by-pass grafting, traumatic shock, organ transplantation, mesenteric, retinal, and peripheral vascular disease, burns, frostbite, re-plantation of limbs and digits, traumatic brain injury, status epilepticus, Parkinson's disease, Huntington's disease, amyotrophic lateral sclerosis, Alzheimer's disease, macular degeneration, acute intracranial hemorrhage, acute renal failure, acute lung injury/adult respiratory distress syndrome, sepsis, meningitis, acute ischemic or alcoholic liver injury, Sjogren's disease, radiation-induced enteritis, and radiation-induced marrow failure.

In the practice of the present invention one or more types of Bcl proteins can be administered to a mammal suffering from inflammation (e.g., suffering from an inflammatory disease, or suffering from an injury that causes inflammation, or undergoing a medical treatment that causes inflammation). Examples of inflammatory diseases include asthma, Crohn's disease, ulcerative colitis, hepatitis (e.g., viral chronic hepatitis), psoriasis, atopic dermatitis, pemphigus, glomerulonephritis, atherosclerosis, sarcoidosis, rheumatoid arthritis, psoriatic arthritis, ankylosing spondylitis, Wegner's syndrome, Goodpasture's syndrome, giant cell arteritis, polyarteritis nodosa, idiopathic pulmonary fibrosis, acute lung injury, chronic obstructive pulmonary disease, post-influenza pneumonia, SARS, tuberculosis, malaria, sepsis, cerebral malaria, Chagas disease, schistosomiasis, bacteria and viral meningitis, cystic fibrosis, multiple sclerosis, Alzheimer disease, encephalomyelitis, sickle cell anemia, pancreatitis, transplantation (e.g., host-mediated rejection of transplanted tissue such as hematopoietic stem cells or an organ, graft mediated host response, such as graft vs. host disease), systemic lupus erythematosis, autoimmune diabetes, thyroiditis, and radiation pneumonitis.

Additionally, in the practice of the present invention one or more Bcl proteins can be administered to a mammal that is not suffering from an inflammatory disease or a disease associated with cell death. For example, one or more types of Bcl proteins can be administered prophylactically to a mammal to prevent, or decrease the likelihood of, the onset of cell death or inflammation, or to reduce the severity of cell death and/or inflammation that may subsequently occur. The mammal may be suffering from a disease that can cause cell death and/or inflammation, and the Bcl protein is administered to prevent, or decrease the likelihood of, the onset of cell death or inflammation, or to reduce the severity of cell death and/or inflammation that may subsequently occur. For example, the following categories of human patients may benefit from administration of Bcl to prevent, or decrease the likelihood of, the onset of cell death or inflammation: patients who suffer from transient ischemic attacks at risk for stroke, patients with unstable angina at risk for myocardial infarction, patients with trauma or burns at risk for multiple organ dysfunction, and patients undergoing cardio-pulmonary by-pass grafting at risk for post-operative organ dysfunction.

As used herein, the term "Bcl protein" refers to a protein that inhibits cell death in a mammal when administered to the mammal, and/or inhibits inflammation in a mammal when administered to the mammal, and that is a member of at least one of the following groups of proteins (identified as Groups (a) through (g)).

Group (a): A protein that includes an amino acid sequence that is at least 35% identical (e.g., at least 40%, or at least 45%, or at least 50%, or at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical)) to the amino acid sequence set forth in SEQ ID NO:1:

```
                                          (SEQ ID NO: 1)
RRVGDELEKEYERAFSSFSAQLHVTPTTARELFGQVATQLF

SDGNINWGRVVALFSEGGFLALKLVDKELEDLVSRLASFLS

EFLAKTLANWLRENGGW.
```

The amino acid sequence set forth in SEQ ID NO:1 is a consensus sequence for the Bcl domain for members of the Bcl-2 family of proteins.

Group (b): A protein that includes at least 12 amino acids, wherein the protein is at least 50% similar (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% similar) to a segment of the Bcl-2 protein consisting of the amino acid sequence set forth in SEQ ID NO:2 (GenBank accession number AAH27258). In some embodiments, the protein is at least 50% similar to the following segment of Bcl-2 protein: TGYDNREIVMKYIHYKLSQR-GYEWD (SEQ ID NO:3). In some embodiments, the protein is at least 50% identical (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical) to a segment of the Bcl-2 protein consisting of the amino acid sequence set forth in SEQ ID NO:2. The Bcl-2 class of proteins are intracellular cytoplasmic proteins that inhibit cell death (see, e.g., J. M. Adams and S. Cory, *Science* 281:1322-1326 (Aug. 28, 1998); S. Cory, et al., *Oncogene* 22:8590-8607, 2003).

Group (c): A protein that includes at least 12 amino acids, wherein the protein is at least 50% similar (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% similar) to a segment of an A-1 protein (also referred to as a Bfl-1 protein), wherein the A-1 protein consists of the amino acid sequence set forth in SEQ ID NO:4 (GenBank accession number AAC50438). In some embodiments, the protein is at least 50% similar to the following segment of A-1 protein: FGYIYRLAQDYLQCVL-QIPQPGSGPSKTSR (SEQ ID NO:5). In some embodiments, the protein is at least 50% identical (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical) to a segment of the A-1 protein consisting of the amino acid sequence set forth in SEQ ID NO:4. A-1 proteins are homologs of Bcl-2 and are intracellular cytoplasmic proteins that inhibit apoptosis (see, e.g., A. Karsan, et al., *Blood* 87(8):3089-3096, Apr. 15, 1996; S. S. Choi et al., *Mammalian Genome* 8:781-782, 1997).

Group (d): A protein that includes at least 12 amino acids, wherein the protein is at least 50% similar (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% similar) to a segment of a Bcl-X protein, wherein the Bcl-X protein consists of the amino acid sequence set forth in SEQ ID NO:6 (GenBank accession number Q07817). In some embodiments, the protein is at least 50% similar to the following segment of Bcl-X protein: MSQSNRELVVD-FLSYKLSQKGYSWSQF (SEQ ID NO:7). In some embodiments, the protein is at least 50% identical (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical) to a segment of the Bcl-X protein consisting of the amino acid sequence set forth in SEQ ID NO:6. Bcl-X proteins are homologs of Bcl-2 and are intracellular cytoplasmic proteins that inhibit apoptosis (see, e.g., L. H. Boise, et al., *Cell* 74(4):597-608, Aug. 27, 1993.

Group (e): A protein that includes at least 12 amino acids, wherein the protein is at least 50% similar (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% similar) to a segment of a Bcl-W protein consisting of the amino acid sequence set forth in SEQ ID NO:8 (GenBank accession number AAB09055). In some embodiments, the protein is at least 50% similar to the following segment of Bcl-W protein: SAPDTRALVADFVGYKL-RQKGYVC (SEQ ID NO:9). In some embodiments, the protein is at least 50% identical (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical) to a segment of the Bcl-W protein consisting of the amino acid sequence set forth in SEQ ID NO:8. Bcl-W proteins are homologs of Bcl-2, and are intracellular cytoplasmic proteins that inhibit apoptosis (see, e.g., L. Gibson, et al., *Oncogene* 13(4):665-675, Aug. 15, 1996).

Group (f): A protein that includes at least 12 amino acids, wherein the protein is at least 50% similar (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% similar) to a segment of an Mcl-1 protein, wherein the Mcl-1 protein consists of the amino acid sequence set forth in SEQ ID NO:10 (GenBank accession number AAF64255). In some embodiments, the protein is at least 50% similar to the following segment of Mcl-1 protein: DLYRQSLEIISRYLREQATG (SEQ ID NO:11). In some embodiments, the protein is at least 50% identical (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical) to a segment of the Mcl-1 protein consisting of the amino acid sequence set forth in SEQ ID NO:10. Mcl-1 proteins are homologs of Bcl-2 and are intracellular cytoplasmic proteins that inhibit apoptosis.

Group (g): A protein that is at least 50% similar (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% similar) to a BH4 domain consisting of the following amino acid sequence: PRLDIRGLVVDYV-TYKLSQNGYEW (SEQ ID NO:12). In some embodiments, the protein is at least 50% identical (e.g., at least 55%, or at least 60%, or at least 65%, or at least 70%, or at least 75%, or at least 80%, or at least 85%, or at least 90%, or at least 95%, or at least 96%, or at least 97%, or at least 98%, or at least 99% identical) to the BH4 domain consisting of the amino acid sequence set forth in SEQ ID NO:12. BH4 (Bcl-2 homology domain 4) is an N-terminal domain found in Bcl-2, Bcl-X, and Bcl-W proteins. The amino acid sequence set forth in SEQ ID NO:12 is a consensus sequence for the BH4 domain of the Bcl-2 family of proteins.

As used herein, the term "protein" includes proteins having at least 12 amino acids.

As used herein in connection with proteins useful in the practice of the present invention, the term "segment" refers to at least 12 contiguous amino acids, and can include the complete amino acid sequence of a protein.

Sequence identity (typically expressed as percent identity) in the context of two protein sequences refers to the number of amino acid residues in the two sequences that are the same when the two sequences are aligned for maximum correspondence over a specified comparison window (e.g., if two protein sequences are aligned, each protein has 100 amino acids, and 75 of the amino acids in the first sequence are the same as, and align with, 75 of the amino acids in the second sequence, then the percent identity is 75%). Sequence identity values provided herein refer to the value obtained using GAP (e.g., GCG programs (Accelrys, Inc., San Diego, Calif.) version 10) using the following parameters: percent identity using GAP Weight of 50 and Length Weight of 3. The entire amino acid sequence of a candidate protein and a reference protein are compared. GAP uses the algorithm of Needleman & Wunsch *J. Mol. Biol.* 48:443-53, 1970, to find the alignment of two complete sequences that maximizes the number of matches and minimizes the number of gaps. An equivalent method to GAP may be used. The term "equivalent method" refers to any sequence comparison method, such as a sequence comparison program, that, for any two sequences in question, generates an alignment having identical amino acid residue matches and an identical percent sequence identity when compared to the corresponding alignment generated by GAP.

Sequence similarity is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (see, e.g., Henikoff, S., and Henikoff, J. G., *Proc. Nat'l Acad. Sci. USA* 89:10915-10919, 1992). For example, sequence similarity can be determined using the ClustalW alignment program for full alignment, single CPU mode, using the GONNET matrix, a gap opening penalty of 100, a gap closing penalty of −1, a gap extending penalty of 0.2 and a gap separation penalty of 4. In the aligned sequences, similarity is defined as two amino acids being identical or having conserved substitutions or having semi-conserved substitutions. The ClustalW alignment program is available, for example, on the Internet at the web page of the European Bioinformatics Institute, Wellcome Trust Genome Campus, Hinxton, Cambridge, CB10 1SD, U.K.

Representative examples of amino acid sequences of Bcl-2 proteins, useful in the practice of the present invention, are set forth in the protein database accessible through the Entrez search tool of the National Center for Biotechnology Information, U.S. National Library of Medicine, 8600 Rockville Pike, Bethesda, Md. 20894, under the following accession numbers (the amino acid sequences of each of the identified Bcl-2 proteins are incorporated herein by reference): AAN17784.1; AAB17352.1; AAC53460.1; AAK15454.1; AAC53458.1; AAB17354.1; AAA82174.1; AAF88137.1; AAC72232.1; CAC10003.1; AAC53459.1; AAA19257.1; CAA57886.1; AAB17353.1; AAB96881.1; CAA58557.1; AAA82173.1; AAC15799.1; AAA51039.1; AAK15455.1; AAK31308.1; AAK31307.1; CAA80657.1; AAF89532.1; AAK31306.1; BAB85856.2; AAP35872.1; AAH19307.1; BAB71819.1; CAA80061.1; AAF33212.1; AAP36940.1; CAA04597.1; AAB07677.1; AAR92491.1; AAA37281.1; AAH68988.1; AAC60701.2; AAK92201.1; CAB92245.1; AAA37282.1; BAC33767.1; AAP47159.1; AAA77686.1; BAA01978.1; BAC37060.1; AAA77687.1; AAA53662.1; CAA29778.1; AAH27258.1; AAO26045.1; AAB53319.1; BAC24136.1; AAA35591.1; CAA78018.1; BAC81344.1; BAD05044.1; AAA51814.1; AAA51813.1; AAN03862.1; CAA57844.1; AAH40369.1; BAB28740.1; BAB62748.1; AAH44130.1; AAH71291.1; AAK81706.1; AAH74505.1; AAO64470.1; BAD32203.1; CAA57845.1; AAO64468.1; AAH74021.1; AAC64200.1; AAB86430.1; AAB09056.1; BAB29912.1; BAB23468.1; AAB09055.1; BAA19666.2; AAH73259.1; CAF93123.1; AAO13177.2; CAF96873.1; AAL35559.1; AAP21091.1; AAB97953.1; AAG02475.1; AAK55419.1; AAH27536.1; AAB97956.1; AAH28762.1; AAB97954.1; AAO89009.1; AAP35767.1; AAH16281.1; AAC50438.1; AAC50288.1; CAG46735.1; AAP36152.1; CAG02784.1; CAA70566.1; AAF89533.1; AAO22992.1; AAA03620.1; CAG46760.1; BAC40796.1; CAA73684.1; BAC53619.1; AAH55592.1; AAH66960.1; AAC48806.1; AAF71267.1; AAH04431.1; AAO74828.1; AAA93066.1; AAA74466.1; CAA58997.1; CAG33700.1; BAB85810.1; AAH14175.1; AAA03619.1; AAF98242.1; AAM74949.1; CAD10744.1; AAF71760.1; AAD13295.1; AAH78835.1; AAA75200.1; AAC60700.2; AAH53380.1; AAH18228.1; BAB28776.1; AAA03622.1; AAD31644.1; AAF36411.1; AAC26327.1; AAM34436.1; CAE54428.1; AAH03839.1; AAH21638.1; AAH05427.1; AAC31790.1; BAC77771.1; AAA74467.1; AAF64255.1; AAP36208.1; AAP35286.1; AAH71897.1; AAH17197.1; AAF74821.1; AAD13299.1; AAG00896.1; AAH78871.1; AAH30069.1; AAAC53582.1;

AAB87418.1; BAC21258.1; AAF09129.1; AAH63201.1; AAK06406.1; AAR84081.1; AAP36565.1; AAP35936.1; AAH06203.1; AAD51719.1; AAD31645.1; and AAC50142.1.

Bcl proteins include, for example, naturally-occurring Bcl proteins, synthetic Bcl proteins that may incorporate non-natural amino acids, and Bcl fusion proteins in which a protein, peptide, amino acid sequence, or other chemical structure, is attached to a portion (e.g., N-terminal or C-terminal) of a Bcl protein. Representative examples of proteins or chemical structures that can be fused to a Bcl protein include: human serum albumin, an immunoglobulin, polyethylene glycol, or other protein or chemical structure that, for example, increases the serum half-life of the Bcl protein, or increases the efficacy of the Bcl protein, or reduces the immunogenicity of the Bcl protein.

The ability of a Bcl protein to inhibit cell death in a mammal, and/or to inhibit inflammation in a mammal, can be assessed, for example, in a mammal subjected to ischemia-reperfusion injury. For example, one or more of the following markers and/or assays may be used to assess the ability of a Bcl protein to inhibit cell death and/or inflammation in a mammal subjected to ischemia-reperfusion injury: 1. Inhibition of inflammation and/or cell death is shown by a reduction in creatine kinase concentration in the plasma or serum of a mammal after ischemia-reperfusion of skeletal muscle (see, e.g., Example 9 herein, and Iwata, A., et al., *Blood* 100:2077, 2002); 2. Inhibition of inflammation and/or cell death is shown by a reduction in infarct size following ischemia-reperfusion of mammalian heart or mammalian brain (see, e.g., Example 10 herein, and Palazzo, A. J., *Am. J. Physiol.* 275:H2300, 1998; Piot, C, *Circulation* 96:1598, 1997); 3. Inhibition of inflammation and/or cell death is shown by a reduction in blood urea nitrogen (BUN) and/or creatine following ischemia-reperfusion of mammalian kidney (see, e.g., Daemen, M., *J. Clin. Invest.* 104:541, 1999; Vukicevic, S., *J. Clin. Invest.* 102:202, 1998); 4. Inhibition of inflammation and/or cell death is shown by a reduction in aspartate aminotransferase (AST) and/or alanine aminotransferase (ALT) following ischemia-reperfusion of mammalian liver (see, e.g., Cursio, R., *FASEB J.* 13:253, 1999); 5. Inhibition of inflammation and/or cell death is shown by an improvement in arterial oxygen content following ischemia-reperfusion of mammalian lung; 6. Inhibition of inflammation and/or apoptosis is shown by a reduction in lung edema following ischemia-reperfusion of mammalian lung (see, e.g., Kowalski, T. F., *J. Appl. Physiol.* 68:125, 1990; 7. Inhibition of cell death is shown by a reduction in markers of cell death (e.g., by reduced DNA strand-breaks assessed by terminal deoxynucleotidyl transferase end labeling (TUNEL), by reduced caspase activation, by increased expression of phosphatidyl serine on the cell surface, by decreased DNA ladder of 180-200 base pair following electrophoresis) in tissue (e.g., skeletal muscle, heart, brain, lung, intestine, kidney, or liver) subjected to ischemia-reperfusion injury (see, e.g., Iwata, et al., *Blood* 100:2077, 2002; Piot, C., *Circulation* 96:1598, 1997; Namura, S., *J. Neurosci.* 18:3659, 1998; Noda, T., *Am. J. Physiol.* 274:G270, 1998; and Cursio, R., *FASEB J.* 13:253, 1999).

Inhibition of inflammation and/or cell death as a result of administration of a Bcl protein can also be assessed in a mammal subjected to sepsis (e.g., sepsis due to cecal ligation and puncture, sepsis due to bacterial pneumonia, sepsis due to bacterial peritonitis), or in a mammal receiving injections or infusions (e.g., injections or infusions into the peritoneum, injections or infusions into the lung, subcutaneous injections or infusions, intra-dermal injections or infusions) of substances that promote sepsis (e.g., lipopolysaccharide, bacterial lipoproteins, lipoteichoic acid). Inhibition of inflammation and/or cell death as a result of administration of a Bcl protein is indicated by increased survival in mammals following initiation of sepsis by the injection or infusion of substances that promote sepsis.

Administration of the Bcl proteins is accomplished by any effective route, e.g., orally or parenterally. Methods of parenteral delivery include topical, intra-arterial, subcutaneous, intramedullary, intravenous, or intranasal administration. Bcl proteins may be administered together with suitable pharmaceutically acceptable carriers including excipients and other compounds that facilitate administration of the Bcl proteins to a mammalian subject. Further details on techniques for formulation and administration may be found, for example, in the latest edition of "Remington's Pharmaceutical Sciences" (Maack Publishing Co, Easton Pa.).

Bcl proteins for oral administration can be formulated using pharmaceutically acceptable carriers well known in the art, in dosages suitable for oral administration. Such carriers enable the Bcl proteins to be formulated as tablets, pills, dragees, capsules, liquids, gels, syrups, slurries, suspensions, etc., suitable for ingestion by a subject.

Bcl proteins for oral use can be obtained, for example, through combination of one or more Bcl proteins with solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Bcl proteins, which can be used orally, can be formulated, for example, as push-fit capsules made of gelatin, as well as soft, sealed capsules made of gelatin and a coating such as glycerol or sorbitol. Push-fit capsules can contain Bcl proteins mixed with filler or binders such as lactose or starches, lubricants such as talc or magnesium stearate, and, optionally, stabilizers. In soft capsules, the Bcl proteins may be dissolved or suspended in suitable liquids, such as fatty oils, liquid paraffin, or liquid polyethylene glycol with or without stabilizers.

Bcl proteins for parenteral administration include aqueous solutions of one or more Bcl proteins. For injection, Bcl proteins may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of Bcl proteins may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the compounds to allow for the preparation of highly concentrated solutions.

For topical or nasal administration, penetrants appropriate to the particular barrier to be permeated are typically used in the formulation. Such penetrants are generally known in the art.

Bcl proteins may be prepared in a form suitable for administration to a mammal by art-recognized techniques (e.g., by means of conventional mixing, dissolving, granulating, dragee-making, levigating, emulsifying, encapsulating, entrapping or lyophilizing processes). The Bcl proteins may also be modified to provide appropriate release characteristics, e.g., sustained release or targeted release, by conventional means (e.g., coating).

The Bcl proteins may be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After such Bcl proteins formulated in an acceptable carrier have been prepared, they can be placed in an appropriate container and labeled for use.

Again by way of representative example, Bcl protein can be introduced into an animal body by application to a bodily membrane capable of absorbing the protein, for example the nasal, gastrointestinal and rectal membranes. The protein is typically applied to the absorptive membrane in conjunction with a permeation enhancer. (See, e.g., V. H. L. Lee, *Crit. Rev. Ther. Drug Carrier Syst.* 5:69, 1988; V. H. L. Lee, *J. Controlled Release* 13:213, 1990; V. H. L. Lee, Ed., *Peptide and Protein Drug Delivery*, Marcel Dekker, N.Y., 1991; DeBoer, A. G., et al., *J. Controlled Release* 13:241, 1990). For example, STDHF is a synthetic derivative of fusidic acid, a steroidal surfactant that is similar in structure to the bile salts, and has been used as a permeation enhancer for nasal delivery. (Lee, W. A., *Biopharm., Nov./Dec.* 22, 1990).

Bcl protein may be introduced in association with another molecule, such as a lipid, to protect the protein from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, 1990). Many polymer systems have been reported for protein delivery (Bae, Y. H., et al., *J. Controlled Release* 9:271, 1989; Hori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 2:235, 1990; Takakura, Y., et al., *J. Pharm. Sci.* 78:117, 1989; Takakura, Y., et al., *J. Pharm. Sci.* 78:219, 1989.)

The amount actually administered will be dependent upon the individual to which treatment is to be applied, and will preferably be an optimized amount such that the desired effect is achieved without significant side-effects. The determination of an effective dose is well within the capability of those skilled in the art. Of course, the skilled person will realize that divided and partial doses are also within the scope of the invention.

For any Bcl protein, the effective dose can be estimated initially in any appropriate animal model (e.g., primate, rats and guinea pigs and other laboratory animals). The animal model is also typically used to achieve a desirable concentration range and route of administration. Such information can then be used to determine useful doses and routes for administration in humans or other mammals.

Therapeutic efficacy and possible toxicity of Bcl proteins can be determined by standard pharmaceutical procedures in experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $ED_{50}/LD_{50}$. Bcl proteins, which exhibit large therapeutic indices, are preferred. The data obtained from animal studies is used in formulating a range of dosage for use in humans or other mammals. The dosage of such compounds lies preferably within a range of circulating concentrations that include the $ED_{50}$ with little or no toxicity. The dosage typically varies within this range depending upon the dosage form employed, sensitivity of the patient, and the route of administration.

Exemplary Bcl dosages include administration of at least 50 ng/kg/day, such as from 50 ng/kg/day to 50 mg/kg/day, or such as from 0.5 mg/kg/day to 50 mg/kg/day, for a period of time sufficient to inhibit cell death and/or inflammation in the mammal. Typically, the Bcl protein is administered to the mammal on multiple occasions (e.g., daily). For example, a Bcl protein can be administered to a mammal at least once per day for a period of from 1 day to 20 days, or from 1 day to 40 days, or from 1 day to 60 days. Bcl protein can be administered indefinitely to a mammalian subject to treat a chronic medical condition (e.g., at least once per day each day during the remaining lifetime of the recipient). The abbreviation "ng" is an abbreviation for nanogram, or nanograms, as appropriate. The abbreviation "mg" is an abbreviation for milligram, or milligrams, as appropriate. The abbreviation "kg" is an abbreviation for kilogram, or kilograms, as appropriate.

In another aspect, the present invention provides methods for identifying a Bcl protein that inhibits cell death and/or inflammation when administered to a mammal. The methods of this aspect of the invention each include the step of screening a plurality of proteins to identify a Bcl protein that inhibits cell death and/or inflammation when administered to a mammal.

In the practice of this aspect of the invention, at least two proteins are screened to identify a Bcl protein that inhibits cell death or inflammation when administered to a mammal. Thus, for example, between two and 100 proteins may be screened to identify a Bcl protein that inhibits cell death or inflammation when administered to a mammal; or, for example, from 100 to 500 proteins may be screened to identify a Bcl protein that inhibits cell death or inflammation when administered to a mammal; or, for example, from 100 to 1000 proteins may be screened to identify a Bcl protein that inhibits cell death or inflammation when administered to a mammal; or, for example, more than 1000 proteins may be screened to identify a Bcl protein that inhibits cell death or inflammation when administered to a mammal.

Any useful assay can be used to identify a protein that inhibits cell death and/or inflammation when administered to a mammal For example, a useful assay can be an in vitro assay, or an in vivo assay, or an assay that includes an in vitro component and an in vivo component. Representative examples of useful assays include the assays described supra for assessing the ability of a Bcl protein to inhibit cell death in a mammal, and/or inhibit inflammation in a mammal subjected to ischemia-reperfusion injury.

In another aspect, the present invention provides methods for identifying a Bcl protein that inhibits cell death or inflammation when administered to a mammal. The methods of this aspect of the invention each include the step of analyzing data obtained from an experiment wherein a plurality of proteins are screened to identify a Bcl protein that inhibits cell death and/or inflammation when administered to a mammal. The analysis can include comparing the effect(s) of candidate Bcl proteins on inflammation and/or cell death in vivo and/or in vitro, and comparing the effect(s) of the candidate proteins to the effects on inflammation and/or cell death of a non-Bcl protein, or a Bcl protein that has been modified (e.g., by site-directed mutagenesis) to be biologically inactive, or to some other control treatment. A statistically significant increase in the amount of inhibition of cell death or inflammation caused by the candidate Bcl protein, compared to the amount of inhibition of cell death and/or inflammation caused by the control treatment, indicates that the candidate Bcl protein inhibits cell death or inflammation. If desired, the candidate Bcl protein may be subjected to further study.

Any of the methods disclosed herein for screening a plurality of Bcl proteins to identify a Bcl protein that inhibits cell death or inflammation in a mammal can be used in this aspect of the invention.

In the practice of this aspect of the invention, the analyzed data are obtained from an experiment wherein a plurality of proteins is screened to identify a Bcl protein that inhibits cell death or inflammation when administered to a mammal. For example, between two and 100 proteins may be screened to identify a Bcl protein that inhibits cell death or inflammation when administered to a mammal; or, for example, from 100 to 500 proteins may be screened to identify a Bcl protein that inhibits cell death or inflammation when administered to a mammal; or, for example, from 100 to 1000 proteins may be screened to identify a Bcl protein that inhibits cell death or inflammation when administered to a mammal; or, for example, more than 1000 proteins may be screened to identify a Bcl protein that inhibits cell death or inflammation when administered to a mammal.

The following examples merely illustrate the best mode now contemplated for practicing the invention, but should not be construed to limit the invention. All literature citations herein are expressly incorporated by reference.

EXAMPLE 1

This Example describes expression of a cDNA (SEQ ID NO:13) that encodes the anti-apoptotic protein, human Bcl-2 (SEQ ID NO:14) in myeloid cells. Expression of the Bcl-2 protein (SEQ ID NO:14) in myeloid cells reduced injury following extended ischemia in the mouse hind limb.

Mice expressing a recombinant human Bcl-2 (SEQ ID NO:14) in their myeloid cells (hMRP8-myeloid-Bcl-2 mice), and control mice that did not express the recombinant human Bcl-2 (SEQ ID NO:14) in their myeloid cells were used in this experiment. The hMRP-myeloid-Bcl-2 mice were previously described by Lagasse, E., and I. L. Weissman, *J. Exp. Mead* 179:1047, 1994, which publication is incorporated herein by reference. These mice were on a C57BL/6 background, and the control mice were C57BL/6 mice.

Mouse skeletal muscle was made ischemic by cross-clamping the aorta distal to the renal artery for 90 minutes, then the clamp was removed and hind limb reperfusion continued for 3 hours. At the end of reperfusion (3 hours after clamp removal) the mice were killed, and the concentration of plasma creatine kinase (CK) was measured and used as an indicator of injury (creatine kinase concentration increases as a result of skeletal muscle injury).

The results of these experiments are shown in FIG. 1. The plasma creatine kinase levels were significantly less in the eleven hMRP8-myeloid-Bcl-2 mice (designated Bcl-2) compared to the nine control C57BL/6 mice (*p<0.05), suggesting that human Bcl-2 (SEQ ID NO:14) protects the mice from ischemia-reperfusion injury. It has been reported in the literature, however, that neutrophils from the hMRP8-myeloid-13c1-2 mice exhibit reduced apoptosis (Lagasse, E., and Weissman, I. L., *J. Exp. Med* 179:1047, 1994), and it is possible that neutrophil apoptosis contributes to ischemia-reperfusion injury by release of toxic products at the site of injury. Thus, it is possible that Bcl-2 is preventing apoptosis of neutrophils, thereby reducing the amount of ischemia-reperfusion injury in the mice that express Bcl-2 in their myeloid cells.

It is unlikely, however, that neutrophils are involved in the ischemia-reperfusion injury for the extended ischemia time of 90 minutes since blocking their emigration into tissue with anti-CD18 mAb has no effect on ischemia-reperfusion injury (Iwata, A. et al., *Blood,* 100:2077 (2002)). Moreover, as shown in Example 2, over-expression of human Bcl-2 (SEQ ID NO:13) in T-lymphocytes also protects against ischemia-reperfusion injury. Thus, it appears to be unlikely that over-expression of human Bcl-2 in myeloid cells is protecting muscle by preventing apoptosis of leukocytes.

EXAMPLE 2

This example shows that over-expression of human Bcl-2 (SEQ ID NO:14) in T-lymphocytes reduces skeletal muscle injury following extended ischemia in the mouse hind limb.

Transgenic mice, on a C57BL/6 genetic background, expressing exogenous human Bcl-2 (SEQ ID NO:14) in their T-cells under the control of the Eµ-promoter (EµT-Bcl-2 mice), and eight C57BL/6 control mice that did not express exogenous Bcl-2 (SEQ ID NO:14) in their T-cells (C57BL/6 mice) were used in this experiment. The EµT-Bcl-2 mice have been previously described and shown to express Bcl-2 (SEQ ID NO:14) only in T-lymphocytes (Strasser, A., et al., *Cell* 67:889, 1991, which publication is incorporated herein by reference).

Figure 2:
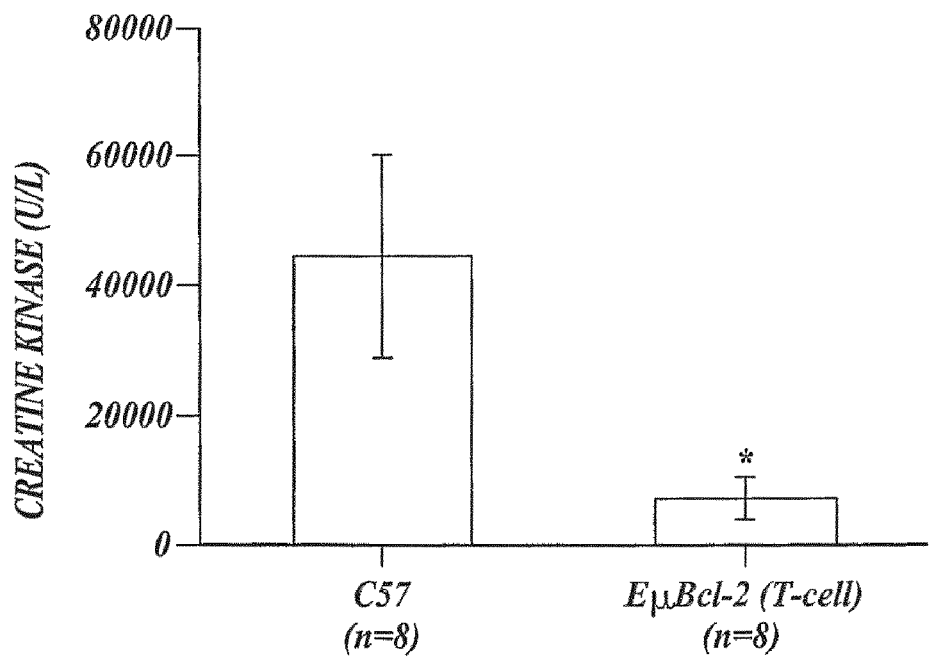
FIG. 2 shows a bar chart of creatine kinase concentration in blood plasma of eight control C57BL/6 mice (identified as C57 in FIG. 2) that had suffered ischemia-reperfusion injury, and a bar chart of creatine kinase concentration in blood plasma of eight EµT-Bcl-2 mice (identified as EµBcl-2 (T-cell) in FIG. 2) that had suffered ischemic injury. ($*p<0.05$).

Hind limb ischemia was induced by cross clamping the aorta as described in Example 1, and ischemia was maintained for 90 minutes followed by 3 hours of reperfusion. Blood samples were taken at the end of the experiment for determination of creatine kinase (CK) concentration in EµT-Bcl-2 mice and C57Bl/6 mice. As shown in FIG. 2, serum CK in the eight EµT-Bcl-2 mice was significantly less than in the eight C57BL/6 control mice (designated C57) (*p<0.05).

EXAMPLE 3

This example shows that over-expression of Bcl-2 (SEQ ID NO:14) in leukocytes reduces DNA strand-breaks in skeletal muscle following extended ischemia and reperfusion of the hind limb.

Transgenic mice (described in Example 2) expressing exogenous human Bcl-2 (SEQ ID NO:14) in their T-cells under the control of the En-promoter (EµT-Bcl-2 mice); transgenic mice expressing exogenous human Bcl-2 (SEQ ID N0:14) in their B-cells under the control of the Eµ-promoter (EµB-Bcl-2 mice) (reported in Strasser, A., *Proc. Natl. Acad. Sci.* 88:8661, 1991); transgenic mice (described in Example 1) expressing exogenous human Bcl-2 (SEQ ID NO:14) in their myeloid cells (hMRP8-myeloid-Bcl-2 mice); and control mice (C57BL/6 mice) that did not express exogenous Bcl-2 (SEQ ID NO:14), were used in this experiment.

It is known that extended ischemia followed by reperfusion of skeletal muscle results in DNA strand-breaks, and that treatment with the caspase inhibitor z-VAD prevents the strand-breaks and reduces the plasma CK concentration (Iwata, A., et al., *Blood* 100:2077, 2002). Tissue from the legs of control mice, EµT-Bcl-2 mice, EµB-Bcl-2 mice and hMRP8-myeloid-Bcl-2 transgenic mice was fixed in formalin and stained to identify DNA strand breaks using the TUNEL technique as described by the manufacturer (In Situ Cell Death Detection Kit, Roche Applied Science, PO Box 50414, 9115 Hague Road, Indianapolis, Ind. 46250-0414).

Figure 3:
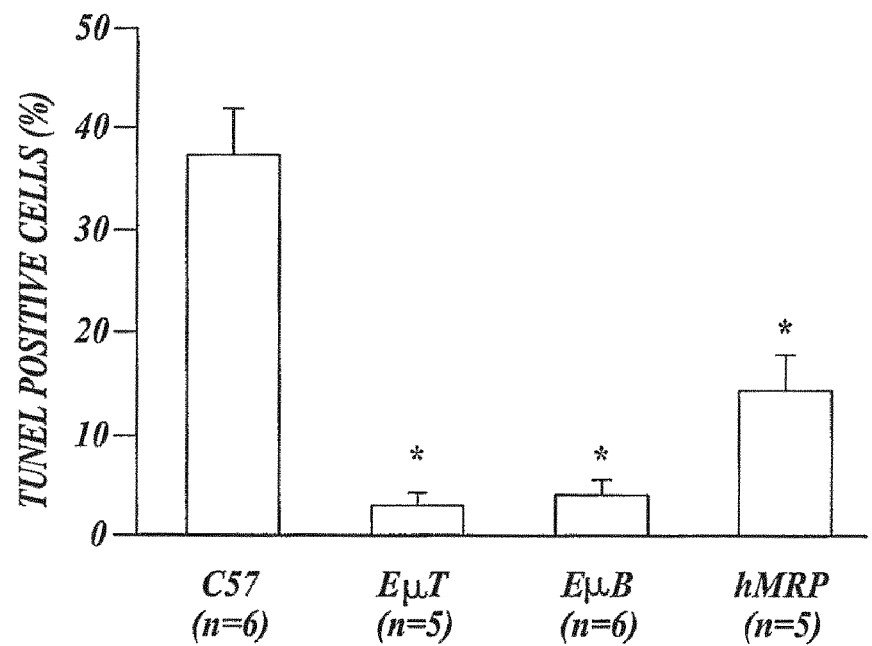
FIG. 3 shows a bar chart of the percentage of TUNEL positive cells in muscle tissue from the legs of six control C57BL/6 mice (abbreviated as C57), five EµT-Bcl-2 mice (abbreviated as EµT) that express hBcl-2 in their T-cells, six EµB-Bcl-2 mice (abbreviated as EµB) that express hBcl-2 in their B-cells, and five hMRP8-myeloid-Bcl-2 mice (abbreviated as hMRP) that express hBcl-2 in their myeloid cells. As described in Example 3, all of the mice had suffered ischemia-reperfusion injury ($*p<0.05$ versus C57).

The number of nuclei that stained positive (indicating the presence of DNA strand breaks) as a percent of the total number of nuclei is shown in FIG. 3 for all four types of mice. The control C57BL/6 mice (designated C57) had significantly more positive nuclei compared with each of the transgenic strains (*$p<0.05$). In the mice that expressed Bcl-2 (SEQ ID NO:14) in one cell type (EµB in B cells, EµT inT cells, or hMRP8 in myeloid cells) DNA strand breaks were prevented in skeletal muscle and endothelial cells, other than the cells that expressed the Bcl-2 (SEQ ID NO:14), suggesting that the cells that expressed Bcl-2 released a molecule that protected cells from DNA strand breaks. That is, protection occurs as a "trans" effect.

EXAMPLE 4

This example shows that blood plasma from mice over-expressing hBcl-2 (SEQ ID NO:14) in T-lymphocytes reduces injury following extended ischemia followed by reperfusion.

Figure 4:
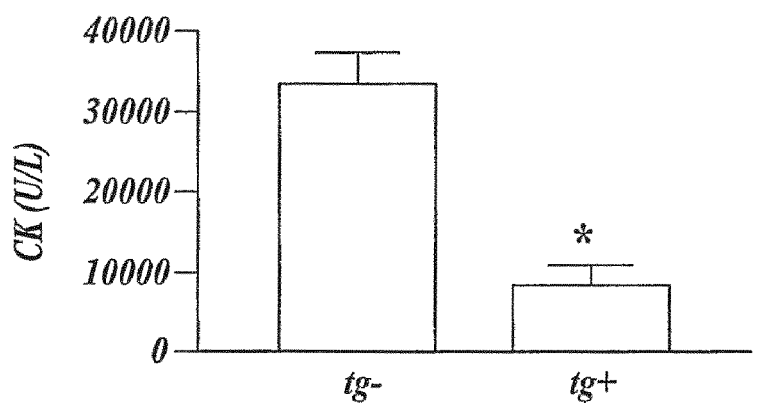
FIG. 4 shows a bar chart of creatine kinase concentration, after ischemia and reperfusion, in blood plasma of six mice (identified as tg+ mice) that had received an injection, before ischemia, of blood plasma extracted from mice that express hBcl-2 in their T-lymphocytes; and a bar chart of creatine kinase concentration, after ischemia and reperfusion, in blood plasma of mice (identified as tg– mice) that had received an injection, before ischemia, of blood plasma extracted from six littermate control mice that did not express hBcl-2 in their T-lymphocytes. ($*p<0.05$).

Transgenic mice (described in Example 2) expressing exogenous human Bcl-2 (SEQ ID NO:14) in their T-lymphocytes (EµT-Bcl-2 mice), and littermate control mice that did not express exogenous human Bcl-2 (SEQ ID NO:14) (C57Bl/6 mice) were used in this experiment. Blood from EµT-Bcl-2 mice and their littermate control mice was drawn into heparin and plasma was extracted by centrifugation. One ml of plasma from EµT-Bcl-2 mice, or one ml of plasma from littermate control mice, was injected into the peritoneum of C57BL/6 mice the day before the mice were subjected to 90 minutes of ischemia and 3 hours of reperfusion as described in Example 1 herein. Blood was drawn from the mice and plasma CK concentration was determined at the end of reperfusion. The results of these experiments are shown in FIG. 4. The six mice that received an injection of plasma from the EµT-Bcl-2 mice (designated tg+) had significantly lower concentrations of CK compared with the six mice that received an injection of plasma from littermate control mice (designated tg−) that did not express exogenous Bcl-2 (SEQ ID NO:14) (*$p<0.05$).

These results show that over-expression of Bcl-2 (SEQ ID NO:14) in the hMRP8-Bcl-2 mice results in the release of a molecule, that acts in "trans", that can be transferred to naive, control, recipient mice and that protects the recipient mice from ischemia-reperfusion injury.

EXAMPLE 5

This example shows that injection of transgenic Jaws II leukocyte cells, that express a cDNA (SEQ ID NO:13) encoding a Bcl-2 protein (SEQ ID NO:14), into mice reduced the amount of ischemia-reperfusion injury compared to control mice that were not injected with Jaws II leukocyte cells.

The recent generation of high efficiency retroviral packaging cell lines, coupled with the development of retroviral expression vectors containing internal ribosome entry site (IRES) elements that allow the expression of two genes from a single mRNA transcript, has provided a new tool for gene transfer into mammalian cells (see, e.g., Hitoshi, Y., et al., *Immunity* 8:461, 1998; Onishi, M., et al., *Exp. Hematol.* 24:324 1996).

A cDNA (SEQ ID NO:13) encoding a hBcl-2 (SEQ ID NO:14) was inserted upstream of the IRES site into the pBM-IRES-EGFP retroviral vector, in which the cDNA for the enhanced green fluorescent protein (EGFP) is cloned downstream of the IRES sequence to produce the pBM-hBcl-2-IRES-EGFP vector. The ecotropic packaging cell line Phoenix was used to produce viral particles to transfect Jaws II cells that were obtained from ATCC. The Phoenix cell line and the retroviral vector are described by Hitoshi, Y., et al., *Immunity* 8:461, 1998, and by Onishi, M., et al., *Exp. Hematol.* 24:324, 1996.

Figure 5:
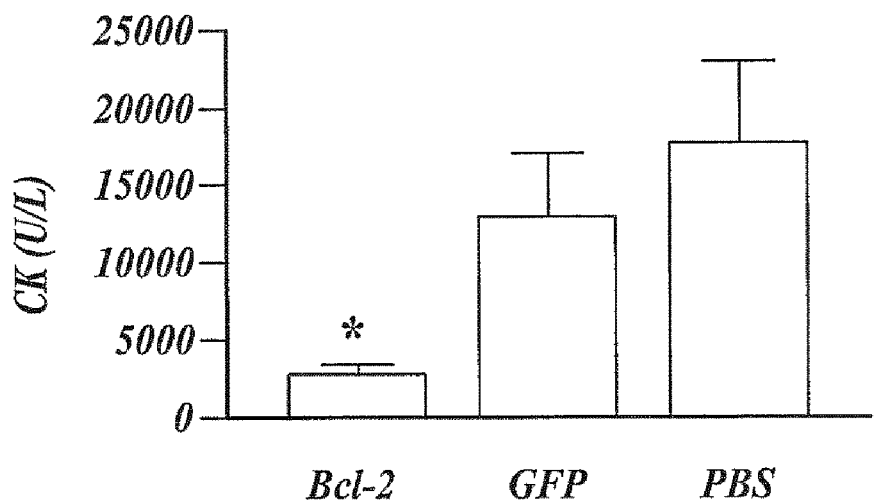
FIG. 5 shows a bar chart of creatine kinase concentration in blood plasma of 18 mice that had been injected with Jaws II leukocytes that express hBcl-2 (identified by the abbreviation Bcl-2); a bar chart of creatine kinase concentration in blood plasma of 16 control mice that had been injected with Jaws II leukocytes that express enhanced green fluorescent protein (identified by the abbreviation GFP); and a bar chart of creatine kinase concentration in blood plasma of 12 control mice that had been injected with phosphate buffered saline (identified by the abbreviation PBS). The creatine kinase concentration was measured after the mice had been subjected to ischemic reperfusion injury as described in Example 5 ($*p<0.05$).

Control Jaws II cells expressed only EGFP. The hBcl-2-JawsII cells or EGFP-JawsII cells were sorted for cells with high expression of EGFP, then injected into C57BL/6 mice the day before subjecting the mice to extended ischemia-reperfusion. As shown in FIG. 5, the 18 mice injected with the hBcl-2-JawsII cells (designated Bcl-2) had significantly lower plasma CK concentration compared with either the 12 mice injected with phosphate buffered saline (designated PBS), or the 16 mice injected with EGFP-JawsII cells (designated GFP). (*$p<0.05$).

EXAMPLE 6

This example shows that the blood plasma CK concentration in mice subjected to ischemic reperfusion injury was lower in mice that had been injected with supernatant from an in vitro culture of hBcl-2-Jaws II cells (that express Bcl-2 (SEQ ID NO:14)), compared to the blood plasma CK concentration in mice that had been injected with supernatant from an in vitro culture of Jaws II cells that expressed enhanced green fluorescent protein (EGFP, EGFP-JawsII cells). The hBcl-2-Jaws II cells and the EGFP-Jaws II cells are described in Example 5.

Figure 6:
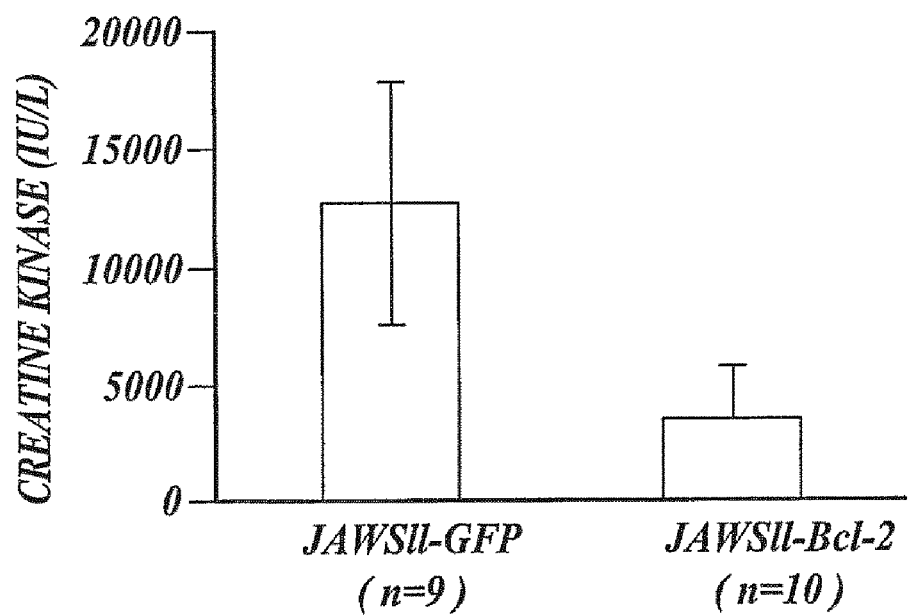
FIG. 6 shows a bar chart of creatine kinase concentration; after ischemia and reperfusion, in blood plasma of ten mice (identified as JAWSII-Bcl-2 in FIG. 6) that had received an injection, before ischemia, of supernatant medium from a culture of hBcl-2-Jaws II cells that express Bcl-2; and a bar chart of creatine kinase concentration, after ischemia and reperfusion, in blood plasma of nine mice (identified as JAWSII-GFP in FIG. 6) that had received an injection, before ischemia, of supernatant medium from a culture of EGFP-Jaws II cells that express enhanced green fluorescent protein. The creatine kinase concentrations were significantly different at $p<0.05$.

Medium from cell cultures of hBcl-2-Jaws II cells and EGFP-Jaws II cells was harvested 24 hours after the start of incubation and concentrated approximately 10-fold using centrifugal filters with a molecular size cut-off of approximately 3 kD. One ml of concentrated Medium from either hBcl-2-Jaws II cells or EGFP-Jaws II cells was injected into the peritoneum of C57BL/6 mice 24 hours prior to extended ischemia-reperfusion. Plasma was extracted from the mice after ischemia-reperfusion, and plasma CK concentration was determined. As shown in FIG. 6, the plasma creatine kinase concentration in ten mice injected with hBcl-2-Jaws II cell supernatant (designated JAWSII-Bcl-2) was significantly less ($p<0.05$) than the plasma creatine kinase concentration in nine mice injected with EGFP-Jaws II cell supernatant (designated JAWSII-GFP).

EXAMPLE 7

This example shows that human Bcl-2 (SEQ ID NO:14) is secreted from cultured JawsII-Bcl-2 cells into the culture supernatant.

Jaws II cells (described in Example 5) expressing either human Bcl-2 (SEQ ID NO:14) or enhanced green fluorescent protein (EGFP) were incubated for 24 hours in serum free medium, and the supernatants were separately collected and concentrated approximately 10 fold. Cells were disrupted in a protease inhibitor cocktail then the lysate and cell supernatant were subjected to immunoblot analysis for Bcl-2. Both the concentrated culture supernatant and the lysate from JawsII-Bcl-2 contained Bcl-2 protein, whereas no Bcl-2 protein was detected in either the concentrated culture supernatant or lysate of JawsII-GFP cells.

EXAMPLE 8

This Example shows that plasma creatine kinase levels in mice that had been subjected to hind leg ischemia and reperfusion was significantly lower in mice that were injected with modified, recombinant, Bcl-2 (SEQ ID NO:15) before hind leg ischemia and reperfusion, compared to the plasma creatine kinase levels in mice that were not injected with recombinant Bcl-2 before hind leg ischemia and reperfusion. SEQ ID NO:15 is a human Bcl-2 that lacks 17 amino acids at the carboxy terminal, and includes a series of 10 histidine residues on the carboxy terminal.

Figure 7:
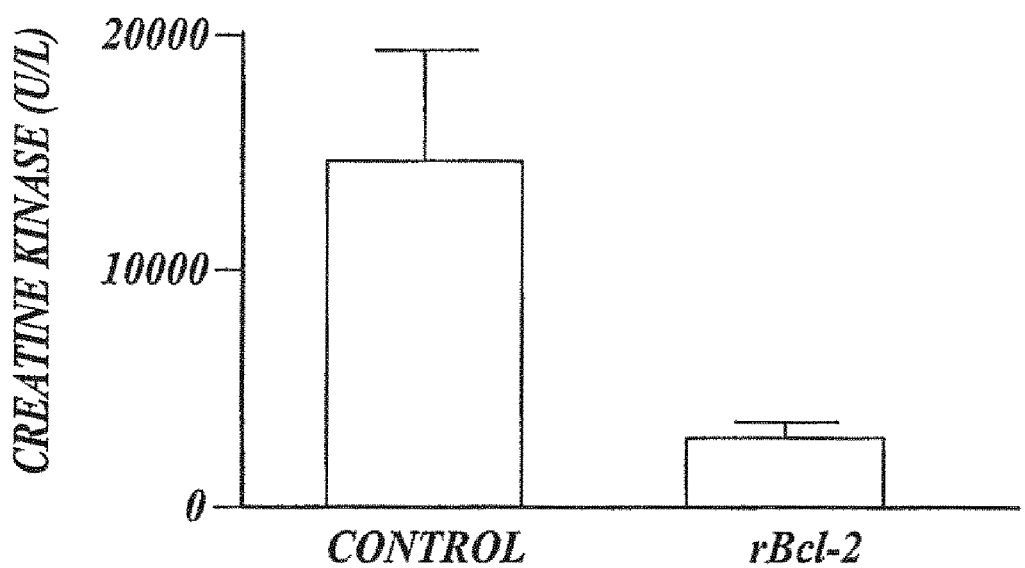
FIG. 7 shows a bar chart of creatine kinase concentration, after ischemia and reperfusion, in blood plasma of 12 mice (identified as rBcl-2) that had received an injection, before ischemia and reperfusion, of recombinant human Bcl-2 (1 µg per mouse); and a bar chart of creatine kinase concentration, after ischemia and reperfusion, in blood plasma of 12 control mice (identified as control) that had received an injection, before ischemia and reperfusion, of either recombinant human ubiquitin or the vehicle solution used for injection of recombinant Bcl-2. There was no difference in the creatine kinase concentration between these two types of controls, and so these control data were combined. The creatine kinase concentrations were significantly different at $p<0.05$.

C57BL/6 mice were injected intraperitoneally with 1 µg per mouse of recombinant human Bcl-2 (rBcl-2) (SEQ ID NO:15) or 1 µg per mouse of recombinant human ubiquitin (rUbiquitin), or the vehicle solution for rBcl-2 the day before the mice were subjected to hind limb ischemia (90 minutes) and reperfusion (180 minutes) as described in Example 1. Blood samples were taken after the 90 minutes of hind limb ischemia and 180 minutes of reperfusion for determination of plasma creatine kinase concentration. There was no difference in the creatine kinase concentration between the two controls (rUbiquitin and vehicle solution) and these data were combined. As shown in FIG. 7, the plasma creatine kinase levels in mice that had been subjected to hind leg ischemia and reperfusion were significantly ($p<0.05$) lower in the 12 mice that were injected with recombinant human Bcl-2 (SEQ ID NO:15) (designated rBcl-2) before hind leg ischemia and reperfusion, compared to the plasma creatine kinase levels in the 12 mice that received rUbiquitin or vehicle solution (designated CONTROL).

EXAMPLE 9

This example shows that over-expression of human Bcl-2 (SEQ ID NO:14) under a myeloid-restricted promoter reduces cardiomyocyte injury following extended ischemia in the mouse heart.

In order to determine whether over-expression of a Bcl-2 protein in leukocytes was protective in tissue other than skeletal muscle, myocardial ischemia-reperfusion injury was examined using ischemia times that were known to be CD18-independent (Palazzo, A. J., et al., *Am. J. Physiol.* 275:H2300, 1998). Control C57BL/6 and hMRP8-Bcl-2 mice were anesthetized, their trachea intubated, and they were placed on mechanical ventilation. A left thoracotomy was performed then an 8-0 suture was passed under the left anterior descending coronary artery (LAD) 2-3 mm from the tip of the left auricle, and the vessel was occluded. Care was taken not to damage the vessel. Occlusion was confirmed visually by change in color. The ligature was carefully removed after 1 hour of occlusion and reperfusion verified by direct visualization as color was re-established. The chest was closed taking care to remove air from the chest, the animal was extubated, given 0.5 ml of warmed saline, and placed in a heated incubator. Two hours later the mice were re-anesthetized, their trachea intubated, and they were placed on mechanical ventilation. The heart was exposed through the original incision and the original 8-0 suture re-tied. The mice were killed by exsanguination and a clamp was placed across the aorta, then 1 ml of 1.5% Evans Blue dye was injected by inserting a 30 gauge needle into the aorta so that the coronary circulation was perfused with dye.

The heart was removed, cut perpendicular to the long axis resulting in 4 sections that were incubated in 5 ml of 1% triphenyltetrazolium chloride (TTC) for 30 minutes. The left ventricle was placed in 10% buffered formaldehyde solution overnight following the removal of both the atrium and the right ventricle. Each heart slice was weighed then visualized under a microscope equipped with a CCD camera. The infarct area (uncolored), area at risk (AAR) (uncolored region plus brick red region) and total left ventricular region (AAR plus Evans Blue stained region) were measured by planimetry. The volume of infarction was estimated by the following equation:

$$V_{infarct} = A_1 W_1 + A_2 W_2 + A_3 W_3 + A_4 W_4$$

Where A1, A2, A3, and A4 are the percent area of infarction in section 1, 2, 3, and 4, respectively and W1, W2, W3, and W4 are the corresponding weight in section 1, 2, 3, and 4, respectively. The volume at risk was calculated in a similar manner using appropriate areas.

Figure 8:
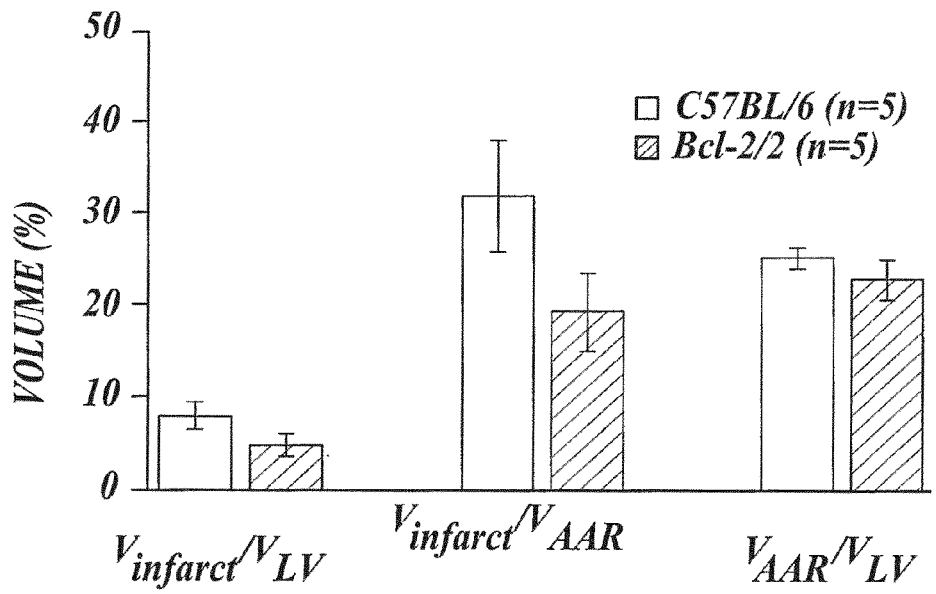
FIG. 8 shows a bar chart of the infarct volume ($V_{infarct}$) as a percentage of the left ventricular volume ($V_{LV}$) for five hMRP8-Bcl-2 mice that express hBcl-2 in their myeloid cells (identified as Bcl-2/2 mice in FIG. 9) and five C57BL/6 control mice; a bar chart of the infarct volume ($V_{infarct}$) as a percentage of the area-at-risk volume ($V_{AAR}$) for C57BL/6 control mice and hMRP8-Bcl-2 mice; and a bar chart of the area-at-risk volume ($V_{AAR}$) as a percentage of the left ventricular volume ($V_{LV}$) for C57BL/6 control mice and hMRP8-Bcl-2 mice. $V_{infarct}/V_{LV}$ and $V_{infarct}/V_{AAR}$ was significantly different between Bcl-2/2 mice and C57BL/6 mice at $p<0.05$.

FIG. 8 shows the infarct volume as a percentage of left ventricular volume and as a percentage of the area at risk volume. The five hMRP8-Bcl-2 mice (designated Bcl-2/2) had reduced infarct volume by both measures compared with the five C57BL/6 control mice, and there were no differences in volume at risk to left ventricular volume between these two groups. $V_{infarct}/V_{LV}$ and $V_{infarct}/V_{AAR}$ of hMRP8-Bcl-2 mice were significantly reduced compared to C57BL/6 ($p<0.05$). There was no difference in volume at risk to left ventricular volume ($V_{AAR}/V_{LV}$) between the two groups.

EXAMPLE 10

This example shows that transgenic mice that express exogenous human Bcl-2 (SEQ ID NO:14) in their T-lymphocytes suffer less cardiomyocyte damage, caused by ischemia followed by reperfusion, than control mice that do not express exogenous Bcl-2 protein (SEQ ID NO:14) in their T-lymphocytes.

Figure 9:
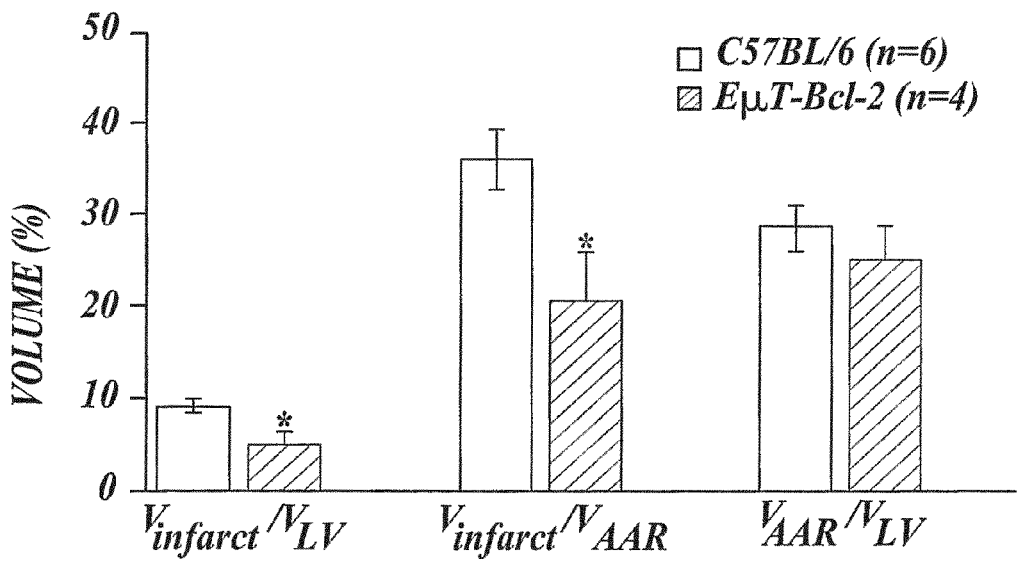
FIG. 9 shows a bar chart of the infarct volume ($V_{infarct}$) as a percentage of the left ventricular volume ($V_{LV}$) for six C57BL/6 control mice and four EµT-Bcl-2 mice (that express Bcl-2 in their T cells); a bar chart of the infarct volume ($V_{infarct}$) as a percentage of the area-at-risk volume ($V_{AAR}$) for C57BL/6 control mice and EµT-Bcl-2 mice; and a bar chart of the area-at-risk volume ($V_{AAR}$) as a percentage of the left ventricular volume ($V_{LV}$) for C57BL/6 control mice and EµT-Bcl-2 mice. $V_{infarct}/V_{LV}$ and $V_{infarct}/V_{AAR}$ was significantly different between EµT-Bcl-2 mice and C57BL/6 mice at $p<0.05$

Additional myocardial ischemia-reperfusion experiments were performed using EµT-Bcl-2 mice that over-expressed Bcl-2 (SEQ ID NO:14) in their T-lymphocytes under the control of the Eµ promoter, and C57BL/6 control mice. The experiments were performed as described in Example 9, with coronary artery occlusion for 1 hour followed by 2 hours of reperfusion. Infarct volume ($V_{infarct}$) was calculated as a percent of left ventricle volume ($V_{LV}$), or as a percent of the volume of the area at risk ($V_{AAR}$). As shown in FIG. 9, $V_{infarct}/V_{LV}$ and $V_{infarct}/V_{AAR}$ were significantly reduced in the Eµ-T-lymphocyte-Bcl-2 mice versus C57BL/6 mice. (*$p<0.05$). There was no difference in volume at risk to left ventricular volume ($V_{AAR}/V_{LV}$) between the two groups.

EXAMPLE 11

This example shows that adoptive transfer of myeloid cells that express exogenous Bcl-2 protein (SEQ ID NO:14) reduces cardiomyocyte injury following extended ischemia in the mouse heart.

hMRP8-myeloid-Bcl-2 mice and littermate control mice were anesthetized, killed and bone marrow was extracted from their long bones. CD11b+ cells in the extracted bone marrow were isolated using magnetic beads (Miltenyi Biotec, 12740 Earhart Avenue, Auburn, Calif. 95602, USA) as described by the manufacturer. Approximately $10^7$ of these cells were administered to C57BL/6 control mice by intraperitoneal injection 18 to 24 hours prior to hind limb ischemia and reperfusion. The ischemic period was 1 hour followed by 2 hours of reperfusion. Determination of infarct size was completed using the same technique as described in Example 9.

Figure 10:
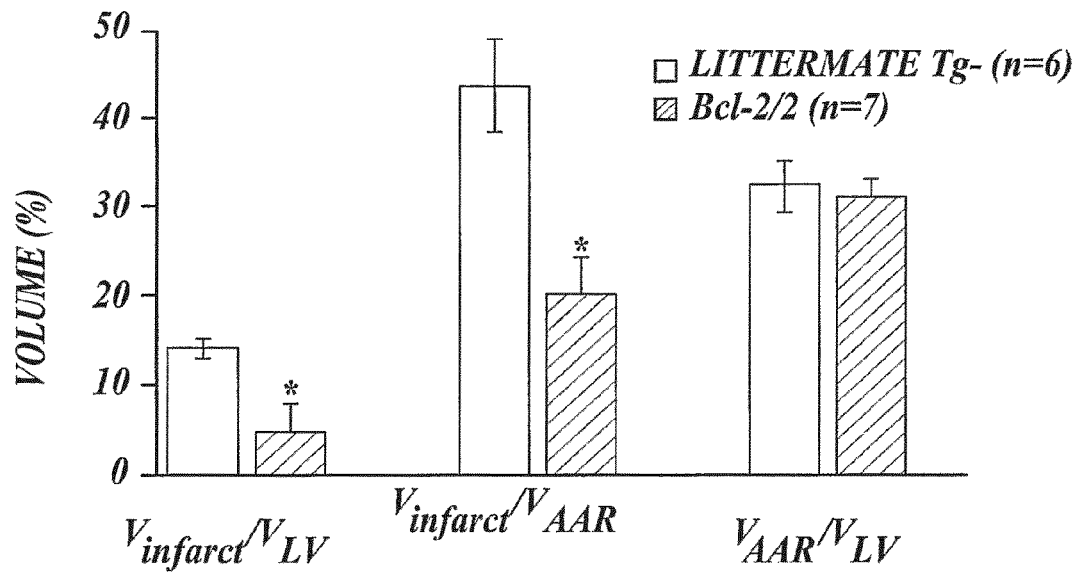
FIG. 10 shows bar charts of the infarct volume ($V_{infarct}$) as a percentage of the left ventricular volume ($V_{LV}$), the infarct volume ($V_{infarct}$) as a percentage of the area-at-risk volume ($V_{AAR}$), and the area-at-risk volume ($V_{AAR}$) as a percentage of the left ventricular volume ($V_{LV}$), for seven C57BL/6 mice that received an injection (before being subjected to myocardial ischemia and reperfusion) of CD11b+ cells that express exogenous human Bcl-2 (these mice are identified as Bcl-2/2 in FIG. 10), and for six C57BL/6 control mice (identified as Littermate Tg-) that had received an infusion (before being subjected to myocardial ischemia and reperfusion) of CD11b+ cells (that did not express exogenous Bcl-2) from their littermates. ($*p<0.05$)

FIG. 10 shows the infarct volume as a percentage of left ventricular volume and as a percentage of the area at risk volume. The seven mice receiving bone marrow cells from the hMRP8-myeloid-Bcl-2 mice (designated Bcl-2/2) had significantly (*p<0.05) reduced infarct volume by both measures ($V_{infarct}/V_{LV}$ and $V_{infarct}/V_{AAR}$) compared with the six mice that received bone marrow cells from littermates (designated littermate Tg−). There was no difference in volume at risk to left ventricular volume ($V_{AAR}/V_{LV}$) between the two groups.

EXAMPLE 12

This example shows that over-expression of Bcl-2 provides protection in septic mice by a "trans" effect.

The survival of transgenic mice that expressed exogenous Bcl-2 (SEQ ID NO:14) in myeloid cells, under control of the human MRP8 promoter (hMRP8-Bcl-2 mice), or in T lymphocytes, under control of the Eµ promoter (EµT-Bcl-2 mice), was compared with the survival of C57BL/6 control mice following cecal ligation and puncture (CLP). 100% of hMRP8-Bcl-2 mice survived CLP, whereas only 25% of control mice survived CLP (p<0.05). In a separate experiment, 87.5% of EµT-Bcl-2 mice survived CLP, whereas only 22.2% of control mice survived CLP (p<0.05).

CD11b-positive bone marrow cells from hMRP8-Bcl-2 mice, or from C57BL/6 mice, were introduced into C57BL/6 mice, which were then subjected to CLP. 100% of the mice that received CD11b-positive bone marrow cells from hMRP8-Bcl-2 mice survived CLP, while none of the mice that received CD11b-positive bone marrow cells from C57BL/6 mice survived CLP.

CD11b-positive bone marrow cells from hMRP8-Bcl-2 mice, or from C57BL/6 mice, were introduced into Rag-1−/− mice (that did not have any mature T or B cells), which were then subjected to CLP. 87.5% of the mice that received CD11b-positive bone marrow cells from hMRP8-Bcl-2 mice survived CLP, while 12.5% of the mice that received CD11b-positive bone marrow cells from C57BL/6 mice survived CLP (p<0.05).

These experiments show that expression of hBcl-2 (SEQ ID NO:14) is protective in CLP and that protection is independent of lymphocytes.

EXAMPLE 13

This example shows that intraperitoneal injection of recombinant human Bcl-2 (SEQ ID NO:15) improves survival in mice subjected to severe sepsis as a result of cecal ligation and puncture.

Figure 11:
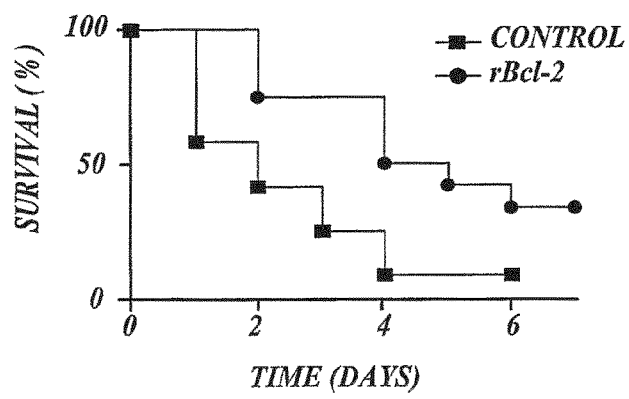
FIG. 11 shows a survival curve for 12 mice that had been injected with recombinant human Bcl-2 (rBcl-2) prior to cecal ligation and puncture, and 12 control mice that were not injected with rBcl-2 prior to cecal ligation and puncture. The survival curves are significantly different at $p<0.05$.

Eight C57BL/6 mice were given an intraperitoneal injection of 1 µg per mouse recombinant human Bcl-2 and eight C57BL/6 mice were given and intraperitoneal injection of 1 µg per mouse recombinant human ubiquitin 12-24 hours prior to being subjected to cecal ligation and puncture as described in Example 12. An additional four C57BL/6 mice were given a subcutaneous injection of 10 µg of a maltose binding protein-hBcl-2 fusion protein and four C57BL/6 mice were given saline treatment 12-24 hours prior to being subjected to cecal ligation and puncture as described in Example 12. The mice were treated with antibiotics twice daily and with an additional treatment of recombinant human Bcl-2 or recombinant human ubiquitin or saline given daily for 3 days. Examination was conducted for signs of irreversible sepsis twice daily for 10 days through the use of a quantitative assessment form, and the mice were killed if they were deemed to be suffering from irreversible sepsis. FIG. 11 is a survival curve based on the results of these experiments and clearly shows that the 12 mice treated with recombinant human Bcl-2 (designated rBcl-2) had significantly (p<0.05) improved survival compared to the 12 mice treated with either recombinant human ubiquitin or saline (designated CONTROL).

EXAMPLE 14

This example shows that plasma creatine kinase levels in mice that had been subjected to hind leg ischemia and reperfusion was significantly lower in mice that were injected with modified recombinant human A1 (human A1 minus 25 amino acids at the carboxy terminal and addition of 6 histidine on the remaining protein) (SEQ ID NO:16) before hind leg ischemia and reperfusion, compared to the plasma creatine kinase levels in mice that were injected with recombinant ubiquitin before ischemia and reperfusion. Recombinant human A1 (SEQ ID NO:16) is a Bcl-2 protein.

C57BL/6 mice were injected intraperitoneally with recombinant human A1 (rA1) (SEQ ID NO:16) or recombinant human ubiquitin (rUbiquitin) the day before the mice were subjected to hind limb ischemia (90 minutes) and reperfusion (180 minutes) as described in Example 1. Blood samples were taken after the 180 minutes of reperfusion for determination of plasma creatine kinase concentration. The plasma creatine kinase levels in mice that had been subjected to hind leg ischemia and reperfusion were significantly (p<0.05) lower in the 12 mice that were injected with rA1 (SEQ ID NO:16) before hind leg ischemia and reperfusion, compared to the plasma creatine kinase levels in 12 control mice that were injected with rUbiquitin.

EXAMPLE 15

This example shows that fragments of a BH4 domain protected the hind-limbs of C57BL/6 mice from ischemia-reperfusion injury.

Skeletal muscle was made ischemic by applying a tourniquet to the hind-limbs of C57BL/6 mice for 90 minutes, then removing the tourniquet and allowing reperfusion for an additional 3 hours. Mice were treated with active peptide 1 (SEQ ID NO:17) or peptide 2 (SEQ ID NO:18) or peptide 3 (SEQ ID NO:19), or with the scrambled (control) peptide (SEQ ID NO:20). Peptide-1 (SEQ ID NO:17) is from the BH4 region of Bcl-2. Peptide-2 (SEQ ID NO:18) is from the first alpha helix of A1. Peptide-3 (SEQ ID NO:19) is from the BH4 region of Bcl-XL. The amino acid sequences of peptide 1 (SEQ ID NO:17), peptide 2 (SEQ ID NO:18), peptide 3 (SEQ ID NO:19), and the scrambled (control) peptide (SEQ ID NO:20) are set forth in Table 1.

TABLE 1

| | | |
|---|---|---|
| TGYDNREIVMKYIHYKLSQRGYEWD | peptide-1 | (SEQ ID NO: 17) |
| FGYIYRLAQDYLQCVLQIPZPGSGP | peptide-2 | (SEQ ID NO: 18) |
| MSQSNRELVVDFLSYKLSQKGYSWSQF | peptide-3 | (SEQ ID NO: 19) |
| TWHMYGNQRDYIGDRSKIVYKLEYE | scrambled peptide | (SEQ ID NO: 20) |

At the end of the 3 hours of reperfusion the mice were killed, and blood was taken for determination of plasma creatine kinase (CK) concentration. The CK concentration was used as an indicator of muscle injury. Elevated levels of CK indicate higher levels of muscle injury. Results from 3 separate experiments showed significant protection compared with the control peptide (p<0.05). The CK concentration for peptide 1 (SEQ ID NO:17) treated mice was 19,020+/−5481 IU/L (n=12) compared with control peptide (SEQ ID NO:20) where CK concentration was 60,530+/−5759 IU/L (n=12). The CK concentration for peptide 2 (SEQ 11) NO:18) treated mice was 33,860+/−5997 IU/L (n=11) compared with control peptide (SEQ ID NO:20) where CK concentration was 69,430+/−11,170 IU/L (n=12). The CK concentration for peptide 3 (SEQ ID NO:19) treated mice was 49,500+/−3,901 IU/L (n=5) compared with control peptide (SEQ ID NO:20) where CK concentration was 80,880+/−11,430 IU/L (n=6).

While the preferred embodiment of the invention has been illustrated and described, it will be appreciated that various changes can be made therein without departing from the spirit and scope of the invention.

The invention claimed is:

1. A method for inhibiting inflammation in a mammal suffering from inflammation, comprising administering to the mammal an isolated protein comprising an amino acid sequence at least 90% similar to the amino acid sequence set forth in SEQ ID NO:18 in an amount sufficient to inhibit inflammation in the mammal, wherein the isolated protein is 25 to 175 amino acids in length.

2. The method of claim 1, wherein the isolated protein comprises the amino acid sequence set forth in SEQ ID NO:18.

3. The method of claim 1, wherein the isolated protein consists of the amino acid sequence set forth in SEQ ID NO:18.

4. The method of claim 1, wherein the isolated protein comprises an amino acid sequence at least 90% similar to the amino acid sequence set forth in SEQ ID NO:16.

5. The method of claim 1, wherein the isolated protein comprises the amino acid sequence set forth in SEQ ID NO:16.

6. The method of claim 1, wherein the isolated protein consists of the amino acid sequence set forth in SEQ ID NO:16.

7. The method of claim 1, wherein the isolated protein comprises an amino acid sequence at least 90% similar to the amino acid sequence set forth in SEQ ID NO:5.

8. The method of claim 1, wherein the isolated protein comprises the amino acid sequence set forth in SEQ ID NO:5.

9. The method of claim 1, wherein the isolated protein consists of the amino acid sequence set forth in SEQ ID NO:5.

10. The method of claim 1, wherein the isolated protein comprises an amino acid sequence at least 90% similar to the amino acid sequence set forth in SEQ ID NO:4.

11. The method of claim 1, wherein the isolated protein comprises the amino acid sequence set forth in SEQ ID NO:4.

12. The method of claim 1, wherein the isolated protein consist of the amino acid sequence set forth in SEQ ID NO:4.

13. The method of claim 1, wherein the mammal is suffering from ischemia of an organ or limb.

14. The method of claim 1, wherein the mammal is suffering from ischemia-repurfusion injury.

15. The method of claim 1, wherein the isolated protein comprises the BH4 domain of the Bcl-2 family of proteins, and wherein the BH4 domain of the Bcl-2 family of proteins is located in the N-terminal domain of the isolated protein.

16. The method of claim 1, wherein the isolated protein is administered transdermally.

17. The method of claim 1, wherein the mammal is suffering from ischemia.

18. The method of claim 1, wherein the isolated protein is administered intravenously, subcutaneously, intraperitoneally, or transdermally.

19. A method for inhibiting inflammation in a mammal suffering from inflammation, comprising administering to the mammal an isolated protein comprising an amino acid sequence at least 90% similar to the amino acid sequence set forth in SEQ ID NO:16 in an amount sufficient to inhibit inflammation in the mammal.

20. The method of claim 19, wherein the isolated protein comprises an amino acid sequence at least 96% similar to the amino acid sequence set forth in SEQ ID NO:16.

* * * * *

SEQUENCE LISTING

```
<160> NUMBER OF SEQ ID NOS: 20

<210> SEQ ID NO 1
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Arg Arg Val Gly Asp Glu Leu Glu Lys Glu Tyr Glu Arg Ala Phe Ser
1               5                   10                  15

Ser Phe Ser Ala Gln Leu His Val Thr Pro Thr Thr Ala Arg Glu Leu
            20                  25                  30

Phe Gly Gln Val Ala Thr Gln Leu Phe Ser Asp Gly Asn Ile Asn Trp
        35                  40                  45

Gly Arg Val Val Ala Leu Phe Ser Phe Gly Gly Phe Leu Ala Leu Lys
    50                  55                  60

Leu Val Asp Lys Glu Leu Glu Asp Leu Val Ser Arg Leu Ala Ser Phe
65                  70                  75                  80

Leu Ser Glu Phe Leu Ala Lys Thr Leu Ala Asn Trp Leu Arg Glu Asn
                85                  90                  95

Gly Gly Trp

<210> SEQ ID NO 2
<211> LENGTH: 239
<212> TYPE: PRT
<213> ORGANISM: Homo sapiens

<400> SEQUENCE: 2

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
            115                 120                 125
```

-continued

Arg Phe Ala Thr Val Val Glu Glu Leu Phe Arg Asp Gly Val Asn Trp
            130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 3
<211> LENGTH: 25
<212> TYPE: PRT
<213> ORGANISM: Homo sapiens

<400> SEQUENCE: 3

Thr Gly Tyr Asp Asn Arg Glu Ile Val Met Lys Tyr Ile His Tyr Lys
1               5                   10                  15

Leu Ser Gln Arg Gly Tyr Glu Trp Asp
                20                  25

<210> SEQ ID NO 4
<211> LENGTH: 175
<212> TYPE: PRT
<213> ORGANISM: Homo sapiens

<400> SEQUENCE: 4

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
                20                  25                  30

Thr Ser Arg Val Leu Gln Asn Val Ala Phe Ser Val Gln Lys Glu Val
            35                  40                  45

Glu Lys Asn Leu Lys Ser Cys Leu Asp Asn Val Asn Val Val Ser Val
50                  55                  60

Asp Thr Ala Arg Thr Leu Phe Asn Gln Val Met Glu Lys Glu Phe Glu
65                  70                  75                  80

Asp Gly Ile Ile Asn Trp Gly Arg Ile Val Thr Ile Phe Ala Phe Glu
                85                  90                  95

Gly Ile Leu Ile Lys Lys Leu Leu Arg Gln Gln Ile Ala Pro Asp Val
            100                 105                 110

Asp Thr Tyr Lys Glu Ile Ser Tyr Phe Val Ala Glu Phe Ile Met Asn
        115                 120                 125

Asn Thr Gly Glu Trp Ile Arg Gln Asn Gly Gly Trp Glu Asn Gly Phe
    130                 135                 140

Val Lys Lys Phe Glu Pro Lys Ser Gly Trp Met Thr Phe Leu Glu Val
145                 150                 155                 160

Thr Gly Lys Ile Cys Glu Met Leu Ser Leu Leu Lys Gln Tyr Cys
                165                 170                 175

<210> SEQ ID NO 5
<211> LENGTH: 30

```
<212> TYPE: PRT
<213> ORGANISM: Homo sapiens

<400> SEQUENCE: 5

Phe Gly Tyr Ile Tyr Arg Leu Ala Gln Asp Tyr Leu Gln Cys Val Leu
1               5                   10                  15

Gln Ile Pro Gln Pro Gly Ser Gly Pro Ser Lys Thr Ser Arg
            20                  25                  30

<210> SEQ ID NO 6
<211> LENGTH: 233
<212> TYPE: PRT
<213> ORGANISM: Homo sapiens

<400> SEQUENCE: 6

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 7
<211> LENGTH: 27
<212> TYPE: PRT
<213> ORGANISM: Homo sapiens

<400> SEQUENCE: 7

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe
            20                  25

<210> SEQ ID NO 8
```

```
<211> LENGTH: 193
<212> TYPE: PRT
<213> ORGANISM: Homo sapiens

<400> SEQUENCE: 8

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys

<210> SEQ ID NO 9
<211> LENGTH: 24
<212> TYPE: PRT
<213> ORGANISM: Homo sapiens

<400> SEQUENCE: 9

Ser Ala Pro Asp Thr Arg Ala Leu Val Ala Asp Phe Val Gly Tyr Lys
1               5                   10                  15

Leu Arg Gln Lys Gly Tyr Val Cys
            20

<210> SEQ ID NO 10
<211> LENGTH: 350
<212> TYPE: PRT
<213> ORGANISM: Homo sapiens

<400> SEQUENCE: 10

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Ser Ala Gly Ala Ser
        50                  55                  60

Pro Pro Ser Thr Leu Thr Pro Asp Ser Arg Arg Val Ala Arg Pro Pro
65                  70                  75                  80
```

```
Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
               100                 105                 110

Ala Pro Ala Ala Asp Ala Ile Met Ser Pro Glu Glu Leu Asp Gly
               115                 120                 125

Tyr Glu Pro Glu Pro Leu Gly Lys Arg Pro Ala Val Leu Pro Leu Leu
130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Asp Leu Tyr Arg
               165                 170                 175

Gln Ser Leu Glu Ile Ile Ser Arg Tyr Leu Arg Glu Gln Ala Thr Gly
               180                 185                 190

Ala Lys Asp Thr Lys Pro Met Gly Arg Ser Gly Ala Thr Ser Arg Lys
               195                 200                 205

Ala Leu Glu Thr Leu Arg Arg Val Gly Asp Gly Val Gln Arg Asn His
210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
               260                 265                 270

Phe Val Ala Lys His Leu Lys Thr Ile Asn Gln Glu Ser Cys Ile Glu
               275                 280                 285

Pro Leu Ala Glu Ser Ile Thr Asp Val Leu Val Arg Thr Lys Arg Asp
               290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
               325                 330                 335

Gly Val Ala Gly Val Gly Ala Gly Leu Ala Tyr Leu Ile Arg
               340                 345                 350

<210> SEQ ID NO 11
<211> LENGTH: 20
<212> TYPE: PRT
<213> ORGANISM: Homo sapiens

<400> SEQUENCE: 11

Asp Leu Tyr Arg Gln Ser Leu Glu Ile Ile Ser Arg Tyr Leu Arg Glu
1               5                   10                  15

Gln Ala Thr Gly
            20

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Arg Leu Asp Ile Arg Gly Leu Val Val Asp Tyr Val Thr Tyr Lys
1               5                   10                  15
```

```
Leu Ser Gln Asn Gly Tyr Glu Trp
            20

<210> SEQ ID NO 13
<211> LENGTH: 720
<212> TYPE: DNA
<213> ORGANISM: Homo sapiens
<220> FEATURE:
<221> NAME/KEY: CDS
<222> LOCATION: (1)..(717)

<400> SEQUENCE: 13 atg gcg cac gct ggg aga agt ggt tac gat aac cgg gag ata gtg atg      48
Met Ala His Ala Gly Arg Ser Gly Tyr Asp Asn Arg Glu Ile Val Met
1               5                   10                  15 aag tac atc cat tat aag ctg tcg cag agg ggc tac gag tgg gat gcg      96
Lys Tyr Ile His Tyr Lys Leu Ser Gln Arg Gly Tyr Glu Trp Asp Ala
                20                  25                  30 gga gat gtg ggc gcc gcg ccc ccg ggg gcc gcc ccc gca ccg ggc ttc     144
Gly Asp Val Gly Ala Ala Pro Pro Gly Ala Ala Pro Ala Pro Gly Phe
            35                  40                  45 ttc tcc tcc cag ccc ggg cac acg ccc cat cca gcc gca tcc cgg gac     192
Phe Ser Ser Gln Pro Gly His Thr Pro His Pro Ala Ala Ser Arg Asp
        50                  55                  60 ccg gtc gcc agg acc tcg cca cta cag acc ccg gct gcc ccc ggc gcc     240
Pro Val Ala Arg Thr Ser Pro Leu Gln Thr Pro Ala Ala Pro Gly Ala
65                  70                  75                  80 gcc gcg ggg cct gcg ctc agc ccg gtg cca cct gtg gtc cac ctg acc     288
Ala Ala Gly Pro Ala Leu Ser Pro Val Pro Pro Val Val His Leu Thr
                85                  90                  95 ctc cgc cag gcc ggc gac gac ttc tcc cgc cgc tac cgc cgc gac ttc     336
Leu Arg Gln Ala Gly Asp Asp Phe Ser Arg Arg Tyr Arg Arg Asp Phe
                100                 105                 110 gcc gag atg tcc agc cag ctg cac ctg acg ccc ttc acc gcg cgg gga     384
Ala Glu Met Ser Ser Gln Leu His Leu Thr Pro Phe Thr Ala Arg Gly
            115                 120                 125 tgc ttt gcc acg gtg gtg gag gag ctc ttc agg gac ggg gtg aac tgg     432
Cys Phe Ala Thr Val Val Glu Glu Leu Phe Arg Asp Gly Val Asn Trp
        130                 135                 140 ggg agg att gtg gcc ttc ttt gag ttc ggt ggg gtc atg tgt gtg gag     480
Gly Arg Ile Val Ala Phe Phe Glu Phe Gly Gly Val Met Cys Val Glu
145                 150                 155                 160 agc gtc aac cgg gag atg tcg ccc ctg gtg gac aac atc gcc ctg tgg     528
Ser Val Asn Arg Glu Met Ser Pro Leu Val Asp Asn Ile Ala Leu Trp
                165                 170                 175 atg act gag tac ctg aac cgg cac ctg cac acc tgg atc cag gat aac     576
Met Thr Glu Tyr Leu Asn Arg His Leu His Thr Trp Ile Gln Asp Asn
            180                 185                 190 gga ggc tgg gat gcc ttt gtg gaa ctg tac ggc ccc agc atg cgg cct     624
Gly Gly Trp Asp Ala Phe Val Glu Leu Tyr Gly Pro Ser Met Arg Pro
        195                 200                 205 ctg ttt gat ttc tcc tgg ctg tct ctg aag act ctg ctc agt ttg gcc     672
Leu Phe Asp Phe Ser Trp Leu Ser Leu Lys Thr Leu Leu Ser Leu Ala
    210                 215                 220 ctg gtg gga gct tgc atc acc ctg ggt gcc tat ctg ggc cac aag tga     720
Leu Val Gly Ala Cys Ile Thr Leu Gly Ala Tyr Leu Gly His Lys
225                 230                 235

<210> SEQ ID NO 14
<211> LENGTH: 239
<212> TYPE: PRT
<213> ORGANISM: Homo sapiens
```

<400> SEQUENCE: 14

```
Met Ala His Ala Gly Arg Ser Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Phe
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Cys Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

<210> SEQ ID NO 15
<211> LENGTH: 222
<212> TYPE: PRT
<213> ORGANISM: Homo sapiens

<400> SEQUENCE: 15

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
```

```
                130                 135                 140
Gly Arg Ile Val Ala Phe Phe Glu Phe Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Asp Ala Phe Val Glu Leu Tyr Gly Pro Ser Met Arg Pro
            195                 200                 205

Leu Phe Asp Phe His His His His His His His His
        210                 215                 220

<210> SEQ ID NO 16
<211> LENGTH: 158
<212> TYPE: PRT
<213> ORGANISM: Homo sapiens

<400> SEQUENCE: 16

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
                20                  25                  30

Thr Ser Arg Val Leu Gln Asn Val Ala Phe Ser Val Gln Lys Glu Val
            35                  40                  45

Glu Lys Asn Leu Lys Ser Cys Leu Asp Asn Val Asn Val Val Ser Val
50                  55                  60

Asp Thr Ala Arg Thr Leu Phe Asn Gln Val Met Glu Lys Glu Phe Glu
65                  70                  75                  80

Asp Gly Ile Ile Asn Trp Gly Arg Ile Val Thr Ile Phe Ala Phe Glu
                85                  90                  95

Gly Ile Leu Ile Lys Lys Leu Leu Arg Gln Gln Ile Ala Pro Asp Val
                100                 105                 110

Asp Thr Tyr Lys Glu Ile Ser Tyr Phe Val Ala Glu Phe Ile Met Asn
            115                 120                 125

Asn Thr Gly Glu Trp Ile Arg Gln Asn Gly Gly Trp Glu Asn Gly Phe
            130                 135                 140

Val Lys Lys Phe Glu Pro Lys Ser His His His His His His
145                 150                 155

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Gly Tyr Asp Asn Arg Glu Ile Val Met Lys Tyr Ile His Tyr Lys
1               5                   10                  15

Leu Ser Gln Arg Gly Tyr Glu Trp Asp
                20                  25
```

```
<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Gly Tyr Ile Tyr Arg Leu Ala Gln Asp Tyr Leu Gln Cys Val Leu
1               5                   10                  15

Gln Ile Pro Glx Pro Gly Ser Gly Pro
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe
            20                  25

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Trp His Met Tyr Gly Asn Gln Arg Asp Tyr Ile Gly Asp Arg Ser
1               5                   10                  15

Lys Ile Val Tyr Lys Leu Glu Tyr Glu
            20                  25
```